US008952132B2

(12) United States Patent
Georgiou et al.

(10) Patent No.: US 8,952,132 B2
(45) Date of Patent: Feb. 10, 2015

(54) ENGINEERED IMMUNOGLOBULIN FC POLYPEPTIDES

(75) Inventors: George Georgiou, Austin, TX (US);
Sang Taek Jung, Austin, TX (US);
William Kelton, Hamilton (NZ); Tae Hyun Kang, Austin, TX (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 13/367,063

(22) Filed: Feb. 6, 2012

(65) Prior Publication Data

US 2012/0208238 A1    Aug. 16, 2012

Related U.S. Application Data

(60) Provisional application No. 61/440,297, filed on Feb. 7, 2011.

(51) Int. Cl.

| C07K 17/00 | (2006.01) |
|---|---|
| C07K 16/00 | (2006.01) |
| C07K 1/00 | (2006.01) |
| C07K 16/28 | (2006.01) |
| C12P 21/08 | (2006.01) |

(52) U.S. Cl.
CPC .......... *C07K 16/283* (2013.01); *C07K 2317/14* (2013.01); *C07K 2317/41* (2013.01); *C07K 2317/732* (2013.01); *C07K 2317/92* (2013.01); *C07K 2319/30* (2013.01)
USPC .......................... 530/350; 530/387.1; 530/395

(58) Field of Classification Search
None
See application file for complete search history.

(56) References Cited

U.S. PATENT DOCUMENTS

| 4,472,509 | A | 9/1984 | Gansow et al. ................ 436/548 |
|---|---|---|---|
| 5,021,236 | A | 6/1991 | Gries et al. ..................... 424/9.34 |
| 5,576,195 | A | 11/1996 | Robinson et al. ............ 435/69.8 |
| 5,578,464 | A | 11/1996 | Lunn et al. ..................... 435/69.1 |
| 5,595,898 | A | 1/1997 | Robinson et al. ........ 435/252.33 |
| 5,618,920 | A | 4/1997 | Robinson et al. ........... 530/387.1 |
| 5,648,260 | A | 7/1997 | Winter et al. ............... 435/252.3 |
| 5,693,493 | A | 12/1997 | Robinson et al. ............ 435/69.1 |
| 5,698,417 | A | 12/1997 | Robinson et al. ............ 435/69.1 |
| 5,698,435 | A | 12/1997 | Robinson et al. ............. 435/328 |
| 5,824,520 | A | 10/1998 | Mulligan-Kehoe ........ 435/91.41 |
| 5,846,818 | A | 12/1998 | Robinson et al. ........... 435/320.1 |
| 5,858,657 | A | 1/1999 | Winter et al. ................ 435/6.14 |
| 5,939,317 | A | 8/1999 | Fayard et al. ............. 435/320.1 |
| 5,994,514 | A | 11/1999 | Jardieu et al. ............ 530/388.22 |
| 6,172,197 | B1 | 1/2001 | McCafferty et al. ....... 530/387.3 |
| 6,204,023 | B1 | 3/2001 | Robinson et al. ............. 435/71.3 |
| 6,248,516 | B1 | 6/2001 | Winter et al. ................ 435/6.16 |
| 6,331,415 | B1 | 12/2001 | Cabilly et al. ............... 435/69.6 |
| 6,455,279 | B1 | 9/2002 | Ambrosius et al. .......... 435/69.1 |
| 6,500,641 | B1 | 12/2002 | Chen et al. ................... 435/69.1 |
| 6,545,142 | B1 | 4/2003 | Winter et al. ............... 536/24.33 |
| 6,555,313 | B1 | 4/2003 | Griffiths et al. .................... 506/9 |
| 6,667,150 | B1 | 12/2003 | Rudert et al. .................... 506/14 |
| 6,696,248 | B1 | 2/2004 | Knappik et al. ............. 435/6.16 |
| 6,737,056 | B1 | 5/2004 | Presta ........................ 424/133.1 |
| 6,806,079 | B1 | 10/2004 | McCafferty et al. ........ 435/320.1 |
| 6,846,653 | B2 | 1/2005 | Kolkman ..................... 435/69.8 |
| 6,979,538 | B2 | 12/2005 | Ladner et al. ................ 435/6.16 |
| 6,979,556 | B2 | 12/2005 | Simmons et al. ............. 435/69.1 |
| 6,989,250 | B2 | 1/2006 | Soderlind et al. ............ 435/91.2 |
| 7,094,571 | B2 | 8/2006 | Harvey et al. ................ 435/69.1 |
| 7,098,302 | B2 * | 8/2006 | Krag et al. ..................... 530/300 |
| 7,118,879 | B2 | 10/2006 | Ladner et al. ..................... 435/9 |
| 7,202,055 | B2 | 4/2007 | Schafer et al. ............... 435/69.1 |
| 7,229,792 | B2 | 6/2007 | Pandiripally ................. 435/69.1 |
| 7,264,963 | B1 | 9/2007 | Knappik et al. ........... 435/320.1 |
| 7,317,091 | B2 | 1/2008 | Lazar et al. ................. 530/387.1 |
| 7,371,826 | B2 | 5/2008 | Presta ........................ 530/387.1 |
| 7,662,925 | B2 | 2/2010 | Lazar et al. ................. 530/387.1 |
| 2003/0180937 | A1 | 9/2003 | Georgiou et al. .............. 506/10 |
| 2004/0132101 | A1 | 7/2004 | Lazar et al. .................... 435/7.1 |
| 2005/0249723 | A1 | 11/2005 | Lazar ........................ 424/133.1 |

(Continued)

FOREIGN PATENT DOCUMENTS

| WO | WO 2008/114011 | * 9/2008 |
|---|---|---|
| WO | WO 2008/137475 | 11/2008 |

(Continued)

OTHER PUBLICATIONS

SEQ ID No. 7 alignment. Jun. 13, 2013. pp. 1-2.*
SEQ ID No. 8 alignment. Jun. 13, 2013. pp. 1-2.*
Huang. Current Opinion in Biotechnology 2009, 20:692-699.*
Berntzen et al., "Prolonged and increased expression of soluble Fc receptors, IgG and a TCR-Ig fusion protein by transiently transfected adherent 293E cells," *J. Immunol. Methods*, 298(1-2):93-104, 2005.
Boruchov et al., "Activating and inhibitory IgG Fc receptors on human DCs mediate opposing functions," *J. Clin. Invest.*, 115910):2914-2923, 2005.

(Continued)

*Primary Examiner* — Chun Dahle
(74) *Attorney, Agent, or Firm* — Parker Highlander PLLC

(57) ABSTRACT

Methods and compositions involving polypeptides having an aglycosylated antibody Fc domain. In certain embodiments, polypeptides have an aglycosylated Fc domain that contains one or more substitutions compared to a native Fc domain. Additionally, some embodiments involve an Fc domain that is binds some Fc receptors but not others. For example, polypeptides are provided with an aglycosylated Fc domain that selectively binds FcγRIIa, but that is significantly reduced for binding to the highly homologous FcγRIIb receptors. Furthermore, methods and compositions are provided for promoting antibody-dependent cell-mediated toxicity (ADCC) using a polypeptide having a modified aglycosylated Fc domain and a second non-Fc binding domain, which can be an antigen binding region of an antibody or a non-antigen binding region. Some embodiments concern antibodies with such polypeptides, which may have the same or different non-Fc binding domain.

18 Claims, 12 Drawing Sheets

(56) References Cited

U.S. PATENT DOCUMENTS

| | | | |
|---|---|---|---|
| 2005/0260736 A1 | 11/2005 | Georgiou et al. | 435/252.3 |
| 2006/0173170 A1 | 8/2006 | Chamberlain et al. | 530/387.3 |
| 2008/0292646 A1 | 11/2008 | Benhar et al. | 424/178.1 |
| 2011/0059075 A1 | 3/2011 | Wittrup et al. | 424/133.1 |

FOREIGN PATENT DOCUMENTS

| | | | |
|---|---|---|---|
| WO | WO 2009/079242 | * | 6/2009 |
| WO | WO 2011/008517 | | 1/2011 |

OTHER PUBLICATIONS

Chames et al., "Direct selection of a human antibody fragment directed against the tumor T-cell epitope HLA-A1-MAGE-A1 from a nonimmunized phage-Fab library," *Proc. Natl. Acad. Sci. USA*, 97:7969-7974, 2000.

Daugherty et al., "Development of an optimized expression system for the screening of antibody libraries displayed on the *Escherichia coli* surface," *Protein Eng.*, 12:613-621 ,1999.

Desai et al., "Characterization of human anti-high molecular weight-melanoma-associated antigen single-chain Fv fragments isolated from a phage display antibody library," *Cancer Res.*, 58:2417-2425, 1998.

Farmer et al., "Penetration of beta-lactamase inhibitors into the periplasm of gram-negative bacteria," *FEMS Microbiol. Lett.*, 176(1):11-5, 1999.

Guzman et al., "Tight regulation, modulation, and high-level expression by vectors containing the arabinose PBAD promoter," *J. Bacteriol.*, 177:4121-4130, 1995.

Harvey et al., "Anchored periplasmic expression, a versatile technology for the isolation of high-affinity antibodies from *Escherichia coli*-expressed libraries, " *Proc. Natl. Acad. Sci. USA*, 101, 9193-9198, 2004.

Hoogenboom and Winter, "By-passing immunisation. Human antibodies from synthetic repertoires of germline VH gene segments rearranged in vitro," *J. Mol. Biol.*, 227(2):381-388, 1992.

Hoogenboom et al., "Antibody phage display technology and its applications," *Immunotechnology.*, 4(1):1-20, 1998.

Jeong and Lee, "Enhanced production of recombinant proteins in *Escherichia coli* by filamentation suppression," *Appl. Environ. Microbiol.*, 69:1295-1298, 2003.

Jung et al., "Aglycosylated IgG variants expressed in bacteria that selectively bind FcgammaRI potentiate tumor cell killing by monocyte-dendritic cells," *Proc. Natl. Acad. Sci. USA* 107(2): 604-609, 2010.

Jung et al., "Efficient expression and purification of human aglycosylated Fc gamma receptors in *Escherichia coli*," *Biotechnology and Bioengineering*, 107(1):21-30, 2010.

Kalergis et al.,"Inducing tumor immunity through the selective engagement of activating Fcgamma receptors on dendritic cells," *Journal of Experimental Medicine*, 195(15):1653-1659, 2002.

Kjaer et al., "Glycerol diversifies phage repertoire selections and lowers non-specific phage absorption,"*FEBS Lett.*, 431(3):448-452, 1998.

Marciano et al., "An aqueous channel for filamentous phage export," *Science*, 284:1516-1519, 1999.

Nikaido, "Multidrug efflux pumps of gram-negative bacteria," *J. Bacteriology*, 178(20):5853-5859, 1996.

Painbeni et al., "Alterations of the outer membrane composition in *Escherichia coli* lacking the histone-like protein HU," *Proc. Natl. Acad. Sci. USA*, 94(13):6712-6717, 1997.

PCT International Search Report and Written Opinion issued in International application No. PCT/US2012/023949, dated May 10, 2012.

Ravetch and Perussia et al., "Alternative membrane forms of Fc gamma RIII(CD16) on human natural killer cells and neutrophils. Cell type-specific expression of two genes that differ in single nucleotide substitutions," *J. Exp. Med.*, 170:481-497, 1989.

Ravetch et al., "Structural heterogeneity and functional domains of murine immunoglobulin G Fc receptors," *Science*, 234:718-725, 1986.

Sazinsky et al., "Aglycosylated immunoglobulin G1 variants productively engage activating Fc receptors," *Proc. Natl. Acad. Sci. USA*, 105(51):20167-20172, 2008.

Wada et al., "A novel labeling approach supports the five-transmembrane model of subunit a of the *Escherichia coli* ATP synthase,"*J. Biol. Chem.*, 274:17353-17357, 1999.

* cited by examiner

Blue: FcγRIIa (PDB: 1FCG)   Gold FcγRIIb (PDB: 2FCB)

```
              Hinge                                  CH2
              220        230       240       250       260       270       280       290
FcWT   (75.76)  [--------]------------------------------------------------------------------ST
Fc5-2a (135.76) [DKTHTCPPC]PAPELLGGPSVFLFPPKPKDTLMISRTPEVTCVVVDVSHEDPEVKFNWYVDGVEVHNAKTKPREEQYNGA
Fc1001 (408.55) [--------]-----------------------------------------------P----------------K----
Fc1002 (303.82) [--------]---------------------------------------------------------------------
Fc1003 (276.75) [--------]---------------------------------------------------------------------
Fc1004 (256.43) [--------]---------------------------------------------------------------------
Fc1005 (231.37) [--------]---------------------------------------------------------------------
Fc1006 (201.20) [--------]---------------------------------------E-----------------------------

CH3
              300       310       320       330       340       350       360       370
FcWT   (75.76)  ----------------------------------------[--------------------------------------
Fc5-2a (135.76) YRVVSVLTVLHQDWLNGKEYKCKVSNKALPAPIEKTISKAK[GQPREPQVYTLPPSRDELTKNQVSLTCLVKGFYPSDIAV
Fc1001 (408.55) ----------------------------------------[--------------------------------------
Fc1002 (303.82) --------------D-------------------------[--------------------------------------
Fc1003 (276.75) ----------------------------------------[--------------------------------------
Fc1004 (256.43) ----------------------------------------[--------------------------------------
Fc1005 (231.37) ----------------------------------------[--------------------------------------
Fc1006 (201.20) ----------------------------------------[--------------------------------------

CH3
              380       390       400       410       420       430       440
FcWT   (75.76)  --E-----------------------------------------M--------------------]
Fc5-2a (135.76) EWVSNGQPENNYKTTPPVLDSDGSFFLYSKLTVDKSRWQQGNVFSCSVIHEALHNHYTQKSLSLSPGK]
Fc1001 (408.55) ---------------------------------------------L-------------------]
Fc1002 (303.82) ---------------------------------------------L-------------------]
Fc1003 (276.75) ------------E----M---------------------------L-------------------]
Fc1004 (256.43) -----------D---------------------------------L-------------------]
Fc1005 (231.37) ---------------------------------------------M-------------------]
Fc1006 (201.20) ---------------------------------------------M-------------------]
```

1) FACS mean values are indicated in the parenthesis

FIG. 6

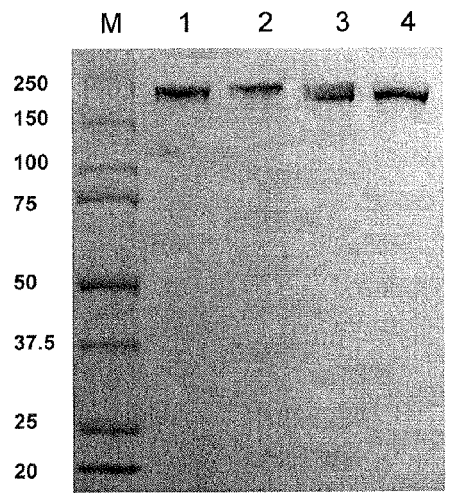
Lane M: Molecular weight standard
Lane 1: AglycoT-Fc1001
Lane 2: AglycoT-Fc1002
Lane 3: AglycoT-Fc1004
Lane 4: AglycoT-Fc2a
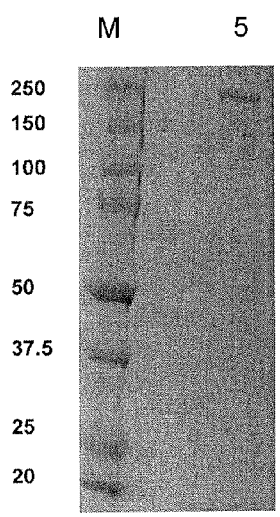
Lane M: Molecular weight standard
Lane 1a: AglycoT-Fc1003
FIG. 9

Lane M: Molecular weight standard

Lane 1: FcγRIIb-strep

Lane 2: FcγRIIb-strep denatured

SEQUENCE LISTING

```
<160> NUMBER OF SEQ ID NOS: 25

<210> SEQ ID NO 1
<211> LENGTH: 227
<212> TYPE: PRT
<213> ORGANISM: Artificial Sequence
<220> FEATURE:
<223> OTHER INFORMATION: Antibody Fc Sequence

<400> SEQUENCE: 1

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95
```

```
Lys Glu Tyr Lys Cys Lys Val Ser Asn Lys Ala Leu Pro Ala Pro Ile
                100                 105                 110
Glu Lys Thr Ile Ser Lys Ala Lys Gly Gln Pro Arg Glu Pro Gln Val
            115                 120                 125
Tyr Thr Leu Pro Pro Ser Arg Asp Glu Leu Thr Lys Asn Gln Val Ser
        130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Lys
225

<210> SEQ ID NO 2
<211> LENGTH: 227
<212> TYPE: PRT
<213> ORGANISM: Artificial Sequence
<220> FEATURE:
<223> OTHER INFORMATION: Antibody Fc Sequence

<400> SEQUENCE: 2

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
                100                 105                 110
Glu Lys Thr Ile Ser Lys Ala Lys Gly Gln Pro Arg Glu Pro Gln Val
            115                 120                 125
Tyr Thr Leu Pro Pro Ser Arg Asp Glu Leu Thr Lys Asn Gln Val Ser
        130                 135                 140
Leu Thr Cys Leu Val Lys Gly Phe Tyr Pro Ser Asp Ile Ala Val Glu
145                 150                 155                 160
Trp Val Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Ile
        195                 200                 205
His Glu Ala Leu His Asn His Tyr Thr Gln Lys Ser Leu Ser Leu Ser
    210                 215                 220
```

Pro Gly Lys
225

<210> SEQ ID NO 3
<211> LENGTH: 227
<212> TYPE: PRT
<213> ORGANISM: Artificial Sequence
<220> FEATURE:
<223> OTHER INFORMATION: Antibody Fc Sequence

<400> SEQUENCE: 3

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Gly Ala Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Val Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Ile
        195                 200                 205

His Glu Ala Leu His Asn His Tyr Thr Gln Lys Ser Leu Ser Leu Ser
    210                 215                 220

Pro Gly Lys
225

<210> SEQ ID NO 4
<211> LENGTH: 227
<212> TYPE: PRT
<213> ORGANISM: Artificial Sequence
<220> FEATURE:
<223> OTHER INFORMATION: Antibody Fc Sequence

<400> SEQUENCE: 4

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser Pro
        35                  40                  45

Glu Asp Pro Glu Val Lys Phe Asn Trp Tyr Val Asp Gly Val Glu Val

```
                50                  55                  60
His Asn Ala Lys Thr Lys Pro Arg Glu Lys Gln Tyr Asn Gly Ala Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Ser Gln Val Ser
    130                 135                 140

Leu Thr Cys Leu Val Lys Gly Phe Tyr Pro Ser Asp Ile Ala Val Glu
145                 150                 155                 160

Trp Val Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Leu
        195                 200                 205

His Glu Ala Leu His Asn His Tyr Thr Gln Lys Ser Leu Ser Leu Ser
    210                 215                 220

Pro Gly Lys
225

<210> SEQ ID NO 5
<211> LENGTH: 227
<212> TYPE: PRT
<213> ORGANISM: Artificial Sequence
<220> FEATURE:
<223> OTHER INFORMATION: Antibody Fc Sequence

<400> SEQUENCE: 5

Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Gly Ala Tyr
 65                  70                  75                  80

Arg Val Val Ser Val Leu Thr Val Leu His Gln Asp Trp Leu Asp Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Val Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
```

```
                    180                 185                 190

Asp Lys Ser Arg Trp Gln Gln Gly Asn Val Phe Ser Cys Ser Val Leu
            195                 200                 205

His Glu Ala Leu His Asn His Tyr Thr Gln Lys Ser Leu Ser Leu Ser
        210                 215                 220

Pro Gly Lys
225

<210> SEQ ID NO 6
<211> LENGTH: 227
<212> TYPE: PRT
<213> ORGANISM: Artificial Sequence
<220> FEATURE:
<223> OTHER INFORMATION: Antibody Fc Sequence

<400> SEQUENCE: 6

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Gly Ala Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Val Ser Asn Gly Gln Pro Glu Asn Asn Tyr Glu Thr Thr Pro Pro
                165                 170                 175

Met Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Leu
        195                 200                 205

His Glu Ala Leu His Asn His Tyr Thr Gln Lys Ser Leu Ser Leu Ser
    210                 215                 220

Pro Gly Lys
225

<210> SEQ ID NO 7
<211> LENGTH: 227
<212> TYPE: PRT
<213> ORGANISM: Artificial Sequence
<220> FEATURE:
<223> OTHER INFORMATION: Antibody Fc Sequence

<400> SEQUENCE: 7

Asp Lys Thr His Thr Cys Pro Pro Cys Pro Ala Pro Glu Leu Leu Gly
1               5                   10                  15
```

```
Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Gly Ala Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Val Ser Asn Gly Gln Pro Glu Asn Asp Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Leu
        195                 200                 205

His Glu Ala Leu His Asn His Tyr Thr Gln Lys Ser Leu Ser Leu Ser
210                 215                 220

Pro Gly Lys
225

<210> SEQ ID NO 8
<211> LENGTH: 227
<212> TYPE: PRT
<213> ORGANISM: Artificial Sequence
<220> FEATURE:
<223> OTHER INFORMATION: Antibody Fc Sequence

<400> SEQUENCE: 8

Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Gly Ala Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140
```

```
Leu Thr Cys Leu Val Lys Gly Phe Tyr Pro Ser Asp Ile Ala Val Glu
145                 150                 155                 160

Trp Val Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 9
<211> LENGTH: 227
<212> TYPE: PRT
<213> ORGANISM: Artificial Sequence
<220> FEATURE:
<223> OTHER INFORMATION: Antibody Fc Sequence

<400> SEQUENCE: 9

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Glu Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Gly Ala Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Val Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 10
<211> LENGTH: 54
<212> TYPE: DNA
<213> ORGANISM: Artificial Sequence
<220> FEATURE:
```

<223> OTHER INFORMATION: Synthetic primer

<400> SEQUENCE: 10
aattcggccc ccgaggcccc tttacccggg gacagggaga ggctcttctg cgtg    54

<210> SEQ ID NO 11
<211> LENGTH: 40
<212> TYPE: DNA
<213> ORGANISM: Artificial Sequence
<220> FEATURE:
<223> OTHER INFORMATION: Synthetic primer

<400> SEQUENCE: 11
ttttaggggt cgacgacaaa actcacacat gcccaccgtg    40

<210> SEQ ID NO 12
<211> LENGTH: 39
<212> TYPE: DNA
<213> ORGANISM: Artificial Sequence
<220> FEATURE:
<223> OTHER INFORMATION: Synthetic primer

<400> SEQUENCE: 12
tttaagggaa gcttctatta ggcgcgccct ttgtcatcg    39

<210> SEQ ID NO 13
<211> LENGTH: 30
<212> TYPE: DNA
<213> ORGANISM: Artificial Sequence
<220> FEATURE:
<223> OTHER INFORMATION: Synthetic primer

<400> SEQUENCE: 13
ggcaaattct gttttatcag accgcttctg    30

<210> SEQ ID NO 14
<211> LENGTH: 27
<212> TYPE: DNA
<213> ORGANISM: Artificial Sequence
<220> FEATURE:
<223> OTHER INFORMATION: Synthetic primer

<400> SEQUENCE: 14
caattttgtc agccgcctga gcagaag    27

<210> SEQ ID NO 15
<211> LENGTH: 62
<212> TYPE: DNA
<213> ORGANISM: Artificial Sequence
<220> FEATURE:
<223> OTHER INFORMATION: Synthetic primer

<400> SEQUENCE: 15
ttttaggggt cgacaagaaa gttgagccca aatcttgtga caaaactcac acatgcccac    60
cg    62

<210> SEQ ID NO 16
<211> LENGTH: 42
<212> TYPE: DNA
<213> ORGANISM: Artificial Sequence
<220> FEATURE:
<223> OTHER INFORMATION: Synthetic primer

<400> SEQUENCE: 16
ggccaccgga tatcttatta tttacccggg gacagggaga gg    42

<210> SEQ ID NO 17
<211> LENGTH: 56
<212> TYPE: DNA
<213> ORGANISM: Artificial Sequence
<220> FEATURE:
<223> OTHER INFORMATION: Synthetic primer

<400> SEQUENCE: 17
ctagggagcc gcgggaggag cagtacaacg gcgcgtaccg tgtggtcagc gtcctc    56

<210> SEQ ID NO 18
<211> LENGTH: 49
<212> TYPE: DNA
<213> ORGANISM: Artificial Sequence
<220> FEATURE:
<223> OTHER INFORMATION: Synthetic primer

<400> SEQUENCE: 18
cgcagcgagg cccagccggc catggcggag gttcaattag tggaatctg    49

<210> SEQ ID NO 19
<211> LENGTH: 29
<212> TYPE: DNA
<213> ORGANISM: Artificial Sequence
<220> FEATURE:
<223> OTHER INFORMATION: Synthetic primer

<400> SEQUENCE: 19
cgacaagaaa gttgagccca aatcttgtg    29

<210> SEQ ID NO 20
<211> LENGTH: 29
<212> TYPE: DNA
<213> ORGANISM: Artificial Sequence
<220> FEATURE:
<223> OTHER INFORMATION: Synthetic primer

<400> SEQUENCE: 20
cacaagattt gggctcaact ttcttgtcg    29

<210> SEQ ID NO 21
<211> LENGTH: 39
<212> TYPE: DNA
<213> ORGANISM: Artificial Sequence
<220> FEATURE:
<223> OTHER INFORMATION: Synthetic primer

<400> SEQUENCE: 21
ttttagggtc tagatcattt acccggggac agggagagg    39

<210> SEQ ID NO 22
<211> LENGTH: 43
<212> TYPE: DNA
<213> ORGANISM: Artificial Sequence
<220> FEATURE:
<223> OTHER INFORMATION: Synthetic primer

<400> SEQUENCE: 22
ctctccacag gcgcgcactc cacacctgca gctcccccaa agg    43

<210> SEQ ID NO 23
<211> LENGTH: 56
<212> TYPE: DNA
<213> ORGANISM: Artificial Sequence
<220> FEATURE:

```
<223> OTHER INFORMATION: Synthetic primer

<400> SEQUENCE: 23
cttatcgtcg tcatccttgt agtcagatcc gggagcttgg acagtgatgg tcacag        56

<210> SEQ ID NO 24
<211> LENGTH: 58
<212> TYPE: DNA
<213> ORGANISM: Artificial Sequence
<220> FEATURE:
<223> OTHER INFORMATION: Synthetic primer

<400> SEQUENCE: 24
ggatctgact acaaggatga cgacgataag gacccgtcta aagatagcaa ggcacaag      58

<210> SEQ ID NO 25
<211> LENGTH: 45
<212> TYPE: DNA
<213> ORGANISM: Artificial Sequence
<220> FEATURE:
<223> OTHER INFORMATION: Synthetic primer

<400> SEQUENCE: 25
atcagcgagc ttctagatca ttagtggtga tgatggtggt gagag                    45
```

ENGINEERED IMMUNOGLOBULIN FC POLYPEPTIDES

This application claims priority to U.S. provisional patent application 61/440,297 filed on Feb. 7, 2011, which is hereby incorporated by reference in its entirety.

BACKGROUND OF THE INVENTION

1. Field of the Invention

The present invention relates generally to the field of protein engineering. More particularly, it concerns improved methods and compositions for the screening of combinatorial antibody Fc libraries expressed in bacteria.

2. Description of Related Art

Currently recombinant therapeutic antibodies have sales of well over $10 bn/yr and with a forecast of annual growth rate of 20.9%, they are projected to increase to $25 bn/yr by 2010. Monoclonal antibodies (mAbs) comprise the majority of recombinant proteins currently in the clinic, with more than 150 products in studies sponsored by companies located worldwide (Pavlou and Belsey, 2005). In terms of therapeutic focus, the mAb market is heavily focused on oncology and arthritis, immune and inflammatory disorders, and products within these therapeutic areas are set to continue to be the key growth drivers over the forecast period. As a group, genetically engineered mAbs generally have higher probability of FDA approval success than small-molecule drugs. At least 50 biotechnology companies and all the major pharmaceutical companies have active antibody discovery programs in place.

The original method for isolation and production of mAbs was first reported at 1975 by Milstein and Kohler (Kohler and Milstein, 1975), and it involved the fusion of mouse lymphocyte and myeloma cells, yielding mouse hybridomas. Therapeutic murine mAbs entered clinical study in the early 1980s; however, problems with lack of efficacy and rapid clearance due to patients' production of human anti-mouse antibodies (HAMA) became apparent. These issues, as well as the time and cost consuming related to the technology became driving forces for the evolution of mAb production technology. Polymerase Chain Reaction (PCR) facilitated the cloning of monoclonal antibodies genes directly from lymphocytes of immunized animals and the expression of combinatorial library of fragments antibodies in bacteria (Orlandi et al., 1989). Later libraries were created entirely by in vitro cloning techniques using naïve genes with rearranged complementarity determining region 3 (CDR3) (Griffiths and Duncan, 1998; Hoogenboom et al., 1998). As a result, the isolation of antibody fragments with the desired specificity was no longer dependent on the immunogenicity of the corresponding antigen. Moreover, the range of antigen specificities in synthetic combinatorial libraries was greater than that found in a panel of hybridomas generated from an immunized mouse. These advantages have facilitated the development of antibody fragments to a number of unique antigens including small molecular compounds (haptens) (Hoogenboom and Winter, 1992), molecular complexes (Chames et al., 2000), unstable compounds (Kjaer et al., 1998) and cell surface proteins (Desai et al., 1998).

In microbial cells, display screening may be carried out by flow cytometry. In particular, Anchored Periplasmic Expression (APEx) is based on anchoring the antibody fragment on the periplasmic face of the inner membrane of *E. coli* followed by disruption of the outer membrane, incubation with fluorescently labeled target and sorting of the spheroplasts (U.S. Pat. No. 7,094,571). APEx was used for the affinity maturation of antibody fragments (Harvey et al., 2004; Harvey et al., 2006). In one study over 200-fold affinity improvement was obtained after only two rounds of screening.

One important mechanism underlying the potency of antibody therapeutics is the ability of antibody to recruit immune cells to a target antigen (or cell). Thus, the Fc region of an antibody is crucial for recruitment of immunological cells and antibody dependent cytotoxicity (ADCC). In particular, the nature of the ADCC response elicited by antibodies depends on the interaction of the Fc region with receptors (FcRs) located on the surface of many cell types. Humans contain five different classes of Fc receptors. In addition haplotypes, or genetic variants of different FcRs belonging to a particular class are known. The binding of an antibody to FcRs determines its ability to recruit other immunological cells and the type of cell recruited. Hence, the ability to engineer antibodies that can recruit only certain kinds of cells can be critically important for therapy.

However, to the inventors' knowledge, previous attempts to engineer Fc domains have been performed using mammalian-expressed IgG molecules. Mammalian antibodies are glycosylated. The carbohydrate chain is attached to the Fc region and alters the conformation of the protein and enables the antibody to bind to FcRs. In contrast, aglycosylated antibodies produced in bacteria cannot bind to FcRs and therefore are unable to elicit ADCC. It is desirable to engineer aglycosylated antibodies that are capable of eliciting ADCC and thus benefit from the lower production costs that are derived from bacterial expression.

Second, and most importantly, mammalian antibodies with engineered Fc regions display increased binding to a particular FcR of interest but in addition they are still capable of binding to other FcRs with normal affinity. Thus, while such antibodies are more selective than the molecules naturally produced by the immune system they can nonetheless still mediate undesirable immunological responses.

Nonetheless, all high throughput antibody screening technologies available to-date rely on microbial expression of antibody fragments. The use of antibody fragments rather than intact or full length IgGs, in the construction and screening of libraries has been dictated by limitations related to the expression of the much larger IgGs in microorganisms. IgG libraries have never before been expressed or screened using microorganisms such as bacteria or yeasts. As a result the isolation of antigen binding proteins has been carried out exclusively using antibody fragments that are smaller and much easier to produce. Once isolated, such antibody fragments have to then be fused to vectors that express full length immunoglobulins which in turn are expressed preferentially in mammalian cells such as CHO cells.

*E. coli* possesses a reducing cytoplasm that is unsuitable for the folding of proteins with disulfide bonds which accumulate in an unfolded or incorrectly folded state (Baneyx and Mujacic, 2004). In contrast to the cytoplasm, the periplasm of *E. coli* is maintained in an oxidized state that allows the formation of protein disulfide bonds. Notably, periplasmic expression has been employed successfully for the expression of antibody fragments such as Fvs, scFvs, Fabs or F(ab')2s (Kipriyanov and Little, 1999). These fragments can be made relatively quickly in large quantities with the retention of antigen binding activity. However, because antibody fragments lack the Fc domain, they do not bind the FcRn receptor and are cleared quickly; thus, they are only occasionally suitable as therapeutic proteins (Knight et al., 1995). Until recently, full-length antibodies could only be expressed in *E. coli* as insoluble aggregates and then refolded in vitro (Boss et al., 1984; Cabilly et al., 1984). Clearly this approach is not amenable to the high throughput screening of antibody libraries since with the current technology it is not possible to refold millions or tens of millions of antibodies individually. A further problem is that since *E. coli* expressed antibodies are not glycosylated, they fail to bind to complement factor 1q (C1q) or Fc and many other Fc receptors. However, aglycosylated Fc domains can bind to the neonatal Fc receptor efficiently (FcRn). Consequently bacterially expressed aglycosylated antibodies do exhibit serum persistence and pharmacokinetics similar to those of fully glycosylated IgGs produced in human cells. Nonetheless, since the aglycosylated antibodies fail to elicit complement activation and can not mediate the recruitment of immune cells such as macrophages, they have previously been ineffective for many therapeutic applications.

In humans there are five major FcγRs. IgG antibodies bind to all these receptors with varying affinities. Of note, out of the 5 FcγRs, four induce activating or pro-inflammatory responses, while one FcγRIIb induces anti-inflammatory or inhibitory responses. All naturally produced antibodies and also recombinant glycosylated antibodies produced by tissue culture contain Fc domains that bind to both the activating and the inhibitory FcγRs. The ability of antibodies to induce activating ADCC depends on the ratio of binding affinities to the activating FcγRs vs the inhibitory FcγRIIb (A/I ratio) (Boruchov et al. 2005; Kalergis et al., 2002). Efforts to enhance the A/I ratio by engineering mutations in glycosylated antibodies that increase binding to activating FcγRs and reduce binding to FcγRIIb have been met with little success to a large part because the latter is 96% homologous to the activating FcγRs. Different FcγR effector functions include (antibody-dependent cell-mediated cytotoxicity (ADCC), cytokine release, phagocytosis, and maturation. Fc domains engineered to have selective effector functions could provide physiological benefits.

SUMMARY OF THE INVENTION

This disclosure provides compounds and methods involving aglycosylated antibody Fc domains that bind to Fc receptors.

In some embodiments, there are compositions involving a polypeptide that has an aglycosylated Fc domain from an antibody ("antibody Fc domain"). In additional embodiments, the aglycosylated Fc domain is a variant of a wild-type Fc domain such that the variation allows the Fc domain to specifically bind to one or more Fc receptors. In some embodiments, a polypeptide with an aglycosylated Fc domain variant is able to bind only a subset of Fc receptors that a polypeptide with glycosylated version of the wild-type Fc domain ("glycosylated wild-type Fc domain") can bind. In specific embodiments, the polypeptide with an aglycosylated Fc domain variant can specifically bind FcγRI; in some cases, it has the affinity or binding ability that is within 2-fold of a polypeptide having a glycosylated wild-type Fc domain. In other embodiments, additionally or alternatively, the polypeptide with an aglycosylated Fc domain variant has significantly reduced affinity or binding ability (50-fold or greater reduction) compared to a polypeptide having a glycosylated wild-type Fc domain. In certain embodiments, the polypeptide with an aglycosylated Fc domain variant has a significantly reduced affinity to or ability to bind FcγRIIb relative to the affinity towards its homologous activating receptor Fc☐RIIa. It is contemplated that a polypeptide may have an affinity or binding ability for FcγRI that is comparable (within 2-fold), as well as significantly reduced affinity or binding ability for FcγRIIB, both as compared to a polypeptide having a glycosylated wild-type Fc domain.

As used herein, the term "affinity" refers to the equilibrium constant for the reversible binding of two agents and is expressed as Kd. Affinity of a binding domain to its target can be, for example, from about 100 nanomolar (nM) to about 0.1 nM, from about 100 nM to about 1 picomolar (pM), or from about 100 nM to about 1 femtomolar (fM); alternatively, it can be between 100 nM and 1 nM or between 0.1 nM and 10 nM. Moreover, it is contemplated that agents specifically bind when there is an affinity between the two agents that is in the affinity ranges discussed above.

An antibody Fc domain may be the Fc domain of an IgA, IgM, IgE, IgD or IgG antibody or a variant thereof. In certain embodiments, the domain is an IgG antibody Fc domain such as an IgG1, IgG2a, IgG2b, IgG3 or IgG4 antibody Fc domain. Furthermore, the antibody Fc domain may be defined as a human Fc domain, in which case it specifically binds one or more human Fc receptors. In certain aspects, the Fc domain may be an IgG1 Fc domain, such as the Fc domain of an anti-HER2 antibody, more specifically, the Fc domain of trastuzumab. It is contemplated that in some embodiments an entire polypeptide is aglycosylated or that in other embodiments only a portion of the polypeptide is aglycosylated, such as the Fe domain. It is also contemplated that a polypeptide may contain one or more regions from an antibody in addition to the Fc domain. A polypeptide may contain an antigen binding domain from an antibody. Moreover, multiple polypeptides may form an antibody or antibody-like protein.

In some embodiments, there is a polypeptide comprising an aglycosylated antibody Fc domain capable of binding a human FcR polypeptide, wherein the Fc domain comprises particular amino acid substitutions. In some embodiments there are multiple amino acid substitutions. With substitutions in the human aglycosylated Fc domain, embodiments include a polypeptide with a human Fc domain having an amino acid substitution at amino acids 298 and 299 and at least one additional substitution at the following position or positions: 382; 382 and 263; 382, 390 and 428; 392, 382, 397 and 428; 315, 382 and 428 or 268, 294, 361, 382 and 428.

In some cases it is contemplated that the substitution at amino acid 298 is glycine (S298G) and the substitution at amino acid 299 is alanine (T299A).

Where the additional amino acid substitution is at amino acid 382, a preferred substitution is valine (E382V).

Where the additional substitution is at amino acids 382 and 263, in preferred embodiments, the substitution at amino acid 382 is valine (E382V) and the substitution at amino acid 263 is glutamic acid (V263E).

Where the additional substitution is at amino acids 382, 390 and 428, in preferred embodiments, the substitution at amino acid 382 is valine (E382V), the substitution at amino acid 390 is aspartic acid (N390D) and the substitution at amino acid 428 is leucine (M428L).

Where the additional amino acid substitution is at amino acids 392, 382, 397 and 428, inn preferred embodiments, the substitution at amino acid 382 is valine (E382V), the substitution at amino acid 392 is glutamic acid (K392E), the substitution at amino acid 397 is methionine (V392M) and the substitution at amino acid 428 is leucine (M428L).

Where the additional amino acid substitution is at amino acids 315, 382 and 428, in preferred embodiments, the substitution at amino acid 315 is aspartic acid (N315D), the substitution at amino acid 382 is valine (E382V), and the substitution at amino acid 428 is leucine (M428L).

Where the additional substitution is at amino acids 268, 294, 361, 382 and 428, in preferred embodiments, the substitution at amino acid 268 is proline (H268P), the substitution at position 294 is lysine (E294K), the substitution at amino acid 361 is serine (N361S), the substitution at amino acid 382 is valine (E382V) and the substitution at amino acid 428 is leucine (M428L).

In some embodiments, a polypeptide has an aglycosylated human Fc domain with a substitution in amino acids 382 and 428 and also has at least one additional substitution in the upper CH2 region.

Embodiments involve a polypeptide having an aglycosylated Fc domain that is capable of specifically binding one or more particular human FcR polypeptides. In some embodiments, the aglycosylated Fc domain has been mutated so that it can bind one or more of FcγRIa, FcγRIIa, FcγRIIb, FcγRIIc, FcγRIIIa, FcγRIIIb, or FcαRI. It is contemplated that the binding to one or more of these particular human FcR polypeptides is within 10, 20, 30, 40, 50, 60, 70, 80, 90, or 100% (or any range derivable therein) of the binding seen with a glycosylated Fc region or that the binding is altered (increased or decreased) by at least or at most 50, 60, 70, 80, 90, or 100% (or any range derivable therein) relative to a wild-type glycosylated Fc domain. Alternatively, relative binding capabilities between polypeptides having a mutated and aglycosylated Fc domain and polypeptides having a glycosylated and wild-type Fc domain may be expressed in terms of X-fold differences (increased or decreased). For example, there may be at least or at most at least 2-, 3-, 4-, 5-, 6-, 7-, 8-, 9-, or 10-fold difference, or any range derivable therein).

In some embodiments, a polypeptide with a mutated aglycosylated Fc domain is capable of specifically binding an FcγRI polypeptide. In some cases, it binds at a level within 2-fold of the level of binding by a polypeptide having a glycosylated and wild-type Fc domain. In other embodiments, the level of binding is within at least 2-, 3-, 4-, 5-, 6-, 7-, 8-, 9-, or 10-fold a glycosylated and wild-type Fc domain. For example, the $K_D$ value for a particular Fc receptor and either a polypeptide with the aglycosylated Fc domain variant or a polypeptide with a glycosylated and wild-type Fc domain is within at least 2- or 3-fold in embodiments described herein. In some embodiments, a polypeptide has at least a 2-fold reduction in pH-dependent FcRn binding compared to polypeptide with an aglycosylated wild-type antibody Fc domain. In additional embodiments, Polypeptides described herein may include a linker in some embodiments. In further embodiments, the linker is a conjugatable linker. In some embodiments, the polypeptide contains an Fc domain from an antibody. It may contain other regions from an antibody, such as another binding domain. The additional binding domain is not an FcR binding domain in certain embodiments. In some embodiments, it may contain an antigen binding site or domain from an antibody. This would include all or part of the variable region from an antibody. In other embodiments, a polypeptide contains an Fc domain from an antibody but another binding domain that is a non-FcR binding domain. In some embodiments, the non-Fc binding region is not an antigen binding site of an antibody but specifically binds a cell-surface protein. In some cases, a cell-surface protein that the non-Fc binding region recognizes is a receptor. In some embodiments, a cell-surface receptor is a tyrosine kinase. In additional embodiments, a polypeptide has a non-Fc binding region capable of binding multiple tyrosine kinase receptors. In some embodiments, such a non-Fc binding region is capable of binding one or more of VEGF receptors, PDGF receptors, EGFR receptors, ErbB-2 receptors, EGF receptors, HGF receptors, and other Src-like tyrosine kinase receptors, or a combination thereof. It is also specifically contemplated that polypeptides have an antigen binding region that recognizes one or more of these receptor tyrosine kinases.

Other polypeptides include those having an aglycosylated Fc domain capable of binding an FcRγI polypeptide and a second binding domain, wherein the second binding domain is capable of specifically binding a cell-surface molecule. In some embodiments, the second binding domain is an antigen binding domain of an antibody ("antibody antigen binding domain"). In some cases, the second binding domain is not an antibody antigen binding domain. In some embodiments, the second binding domain is capable of specifically binding a cell-surface molecule that is a proteinaceous molecule. The second binding domain may be a ligand for a cell-surface receptor or it may be a receptor for a cell-surface ligand.

Embodiments also concern a nucleic acid that encodes any of the polypeptides discussed herein. The nucleic acid may be isolated and/or recombinant. It may be a nucleic acid segment that is isolated and/or recombinant. In some embodiments, the nucleic acid is DNA while in others it is RNA. In certain embodiments, the nucleic acid is a DNA segment. In other embodiments, the nucleic acid is an expression vector that is capable of expressing any of the polypeptides having an Fc binding domain with one or more substitutions that specifically binds a human FcR polypeptide. A nucleic acid may encode one or more polypeptides discussed above, which, depending on how the polypeptide is produced may or may not be glycosylated.

In some embodiments, there are nucleic acids encoding a polypeptide with an Fc domain capable of specifically binding a human FcR polypeptide. The nucleic acid may be placed in a host cell that can express the polypeptide, particularly an aglycosylated version of the polypeptide. The host cell may be a prokaryotic cell, such as a bacterial cell. Alternatively, the host cell may be an eukaryotic cell, such as a mammalian cell. In some embodiments, a host cell contains a first expression vector, though it may comprises a second expression vector as well. Because some antibodies are made of multiple polypeptides, a host cell that expresses these polypeptides is contemplated in some embodiments. For example, in some embodiments there is a host cell that includes a second expression vector that encodes a polypeptide comprising an immunoglobulin light chain.

In some embodiments, there is a population of host cells, wherein the population contains a plurality of host cells that express polypeptides having different Fc domains. It is contemplated that the amino acid sequence of any two different Fc domains differs in identity by less than 20%, 15%, 10%, 5% or less.

In some embodiments there are methods of making the polypeptides described herein (polypeptides having an aglycosylated Fc region) as well as methods of using these polypeptides. Any of these methods may be implemented with respect to any of the polypeptides described herein.

In some embodiments there are methods for preparing an aglycosylated polypeptide comprising: a) obtaining a host cell capable of expressing an aglycosylated antibody comprising an Fc domain capable of binding an FcR polypeptide, wherein the Fc domain comprises an above-mentioned substitution, that is, an amino acid substitution at amino acids 298 and 299 and at least one additional substitution at the following position or positions: 382; 382 and 263; 382, 390 and 428; 392, 382, 397 and 428; 315, 382 and 428 or 268, 294, 361, 382 and 428; b) incubating the host cell in culture under conditions to promote expression of the aglycosylated antibody; and, c) purifying expressed antibody from the host cell. In some embodiments, the host cell is a prokaryotic cell, such as a bacterial cell. In further embodiments, methods involve collecting expressed antibody from the supernatant, which may be done prior to purification.

In some embodiments methods involve purifying the antibody from the supernatant. This may involve subjecting the antibodies from the supernatant to filtration, HPLC, anion or cation exchange, high performance liquid chromatography (HPLC), affinity chromatography or a combination thereof. In some embodiments, methods involve affinity chromatography using staphylococcal Protein A, which binds the IgG Fc region. Other purification methods are well known to those of ordinary skill in the art.

In some embodiments, the aglycosylated polypeptide or antibody is capable of specifically binding an activating FcR polypeptide, which refers to an FcR polypeptide that activates one or more immune cells. Activating polypeptides include FcγRI, IIa, IIIa, IIb, and IIIc. FcγRIIb is an inhibitory FcR polypeptide. In further embodiments, the aglycosylated polypeptide or antibody no longer binds an inhibitory FcR polypeptide at a level comparable to a glycosylated, wild-type Fc domain. In specific embodiments, an aglycosylated polypeptide or antibody specifically binds an FcγRI polypeptide. In further embodiments, the aglycosylated polypeptide or antibody has a reduced capability to bind an FcγRIIb polypeptide, wherein its affinity is at least 50-fold less than a glycosylated, wild-type version of the polypeptide or antibody. In certain embodiments, the aglycosylated antibody is an aglycosylated version of a therapeutic antibody, which refers to an antibody used in therapy or treatment for a disease or condition. Any antibody or polypeptide discussed herein, including those discussed above, may be used in implementing methods for inducing an immune response. An example of a therapeutic antibody is trastuzumab.

In some embodiments, methods involve bacterial cells that are *E. coli* cells. In additional embodiments, the Fc domain is an IgG, IgA or IgE Fc domain. In further embodiments, the population of Gram negative bacterial cells comprise a plurality of nucleic acids encoding the plurality of aglycosylated Fc domains. In some cases the plurality of nucleic acids further encodes a membrane secretion signal fused to the plurality of aglycosylated Fc domains. A membrane secretion signal may be PelB or DsbA. Additionally, the aglycosylated Fc domain may include a hinge, CH2 and CH3 region. In certain embodiments, the aglycosylated polypeptide comprises an eukaryotic FcR domain. In some embodiments, there is a polypeptide with an Fc domain that specifically binds one of the polypeptides of Table 1. In certain embodiments, the Fc domain binds human FcγRIa, FcγRIIa, FcγRIIb, FcγRIIc, FcγRIIIa, FcγRIIIb, FcαRI or C1q. In other embodiments, it has reduced binding affinity for FcγRIIb relative to a glycosylated and wild-type version of the Fc domain. Specific methods are disclosed in WO 2008/137475, which is hereby incorporated by reference.

Other embodiments involve methods for optimizing Fc binding to one or more specific FcR polypeptides of an aglycosylated polypeptide having an Fc domain comprising: a) obtaining a population of Gram negative bacterial cells, cells of which population express a aglycosylated polypeptide comprising an Fc domain in their periplasm, wherein the population expresses a plurality of different polypeptides expressing different mutated Fc domains; b) contacting the bacterial cells with a first FcR polypeptide under conditions to allow contact between the FcR polypeptide and the aglycosylated Fc domains, wherein the FcR polypeptide is FcγRIa, FcγRIIa, FcγRIIb, FcγRIIc, FcγRIIIa, FcγRIIIb, or FcαRI; and c) selecting at least one bacterial cell based on binding of the aglycosylated Fc domain to the first FcR polypeptide. Any of the embodiments discuss above may apply to the implementation of these methods.

Embodiments discussed in the context of a methods and/or composition of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan however these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 5. Error Prone PCR library construction procedure to randomize the Fc region of trastuzumab-Fc5-2a.

FIG. 6. Sequences of isolated aglycosylated trastuzumab Fc variants exhibiting high binding affinity to FcγRIIa over FcγRIIb. Spheroplasts were incubated with 20 nM of FcγRIIa-GST-Alexa488 and 100 nM of FcγRIIb-GST for detection. FACS mean values are indicated in the parenthesis.

FIG. 9. SDS-PAGE gels showing the purified aglycosylated Fc2a, aglycosylated Fc1001, aglycosylated Fc1003, aglycosylated Fc1002 and aglycosylated Fc1004 produced in HEK293 cells. Lane M: molecular weight standard; lane 1: Fc1001; lane 2: Fc1002; lane 3: Fc1004; lane 4: Fc2a; lane 1a: Fc1003.

DESCRIPTION OF ILLUSTRATIVE EMBODIMENTS

Figure 1:
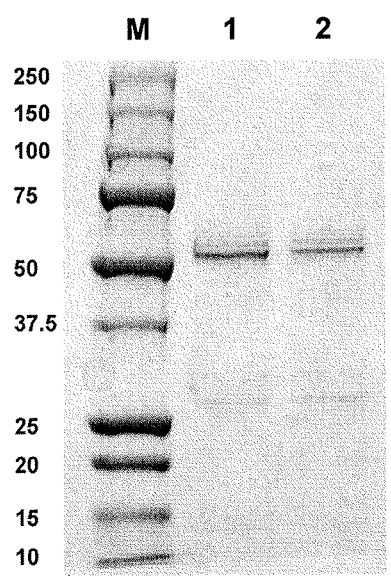
FIG. 1. SDS-PAGE gel showing the purified Fc fragments, wild type Fc and Fc2a proteins. Lane M: molecular weight standards; lane 1: Wild type Fc; lane 2; Fc2a (S298G/T299A).

The inventors previously overcame several major problems with current immunotherapeutic technologies in providing aglycosylated antibody Fc domains that are able to bind to Fc receptor polypeptides. Additional Fc domains with engineered properties have been developed. Further embodiments and advantages are described below, though information about Fc libraries and screening methods are provided.

I. Periplasmic Expression

In some embodiments, polypeptide comprising an antibody Fc domain may be expressed in the periplasmic space of a gram negative bacteria. Furthermore, in some aspects an antibody Fc domain may be anchored to the periplasmic face of the inner membrane. For example, an Fc domain may be directly fused to a membrane spanning or membrane bound polypeptide or may interact (e.g., via protein-protein interactions) with a membrane spanning or membrane bound polypeptide. Such a technique may be termed "Anchored Periplasmic Expression" or "APEx".

The periplasmic compartment is contained between the inner and outer membranes of Gram negative cells (see, e.g., Oliver, 1996). As a sub-cellular compartment, it is subject to variations in size, shape and content that accompany the growth and division of the cell. Within a framework of peptidoglycan heteroploymer is a dense mileau of periplasmic proteins and little water, lending a gel-like consistency to the compartment (Hobot et al., 1984; van Wielink and Duine, 1990). The peptidoglycan is polymerized to different extents depending on the proximity to the outer membrane, close-up it forms the murein sacculus that affords cell shape and resistance to osmotic lysis.

The outer membrane (see Nikaido, 1996) is composed of phospholipids, porin proteins and, extending into the medium, lipopolysaccharide (LPS). The molecular basis of outer membrane integrity resides with LPS ability to bind divalent cations ($Mg^{2+}$ and $Ca^{2+}$) and link each other electrostatically to form a highly ordered quasi-crystalline ordered "tiled roof" on the surface (Labischinski et al., 1985). The membrane forms a very strict permeability barrier allowing passage of molecules no greater than around 650 Da (Burman et al., 1972; Decad and Nikaido, 1976) via the porins. The large water filled porin channels are primarily responsible for allowing free passage of mono and disaccharides, ions and amino acids in to the periplasm compartment (Nikaido and Nakae, 1979; Nikaido and Vaara, 1985). With such strict physiological regulation of access by molecules to the periplasm it may appear, at first glance, inconceivable that large ligands (i.e., larger than the 650 Da exclusion limit) could be employed in screening methods. However, the inventors have shown that ligands greater than 2000 Da in size can diffuse into the periplasm without disruption of the periplasmic membrane. Such diffusion can be aided by one or more treatments of a bacterial cell, thereby rendering the outer membrane more permeable, as is described herein below.

Method for expressing polypeptides and in particular antibodies in the periplasmic space are known in the art for example see U.S. Pat. No. 7,094,571 and U.S. Patent Publ. 20030180937 and 20030219870 each incorporated herein by reference. In some cases, a gram negative bacterial cell of the invention may be defined as an *E. coli* cell. Furthermore, in some aspects a Gram negative bacterial cell may be defined as a genetically engineered bacterial cell such as a Jude-1 strain of *E. coli*.

II. Permeabilization of the Outer Membrane

In some embodiments, methods involve disrupting, permeablizing or removing the outer membrane of bacteria are well known in the art, for example, see U.S. Pat. No. 7,094,571. For instance, prior to contacting the bacterial cells with an FcR polypeptide the outer membrane of the bacterial cell may be treated with hyperosmotic conditions, physical stress, lysozyme, EDTA, a digestive enzyme, a chemical that disrupts the outer membrane, or by infecting the bacterium with a phage or a combination of the foregoing methods. Thus, in some cases, the outer membrane may be disrupted by lysozyme and EDTA treatment. Furthermore, in certain embodiments, the bacterial outer membrane may be removed entirely.

In one embodiment, methods are employed for increasing the permeability of the outer membrane to one or more labeled ligands. This can allow screening access of labeled ligands otherwise unable to cross the outer membrane. However, certain classes of molecules, for example, hydrophobic antibiotics larger than the 650 Da exclusion limit, can diffuse through the bacterial outer membrane itself, independent of membrane porins (Farmer et al., 1999). The process may actually permeabilize the membrane on so doing (Jouenne and Junter, 1990). Such a mechanism has been adopted to selectively label the periplasmic loops of a cytoplasmic membrane protein in vivo with a polymyxin B nonapeptide (Wada et al., 1999). Also, certain long chain phosphate polymers (100 Pi) appear to bypass the normal molecular sieving activity of the outer membrane altogether (Rao and Torriani, 1988).

Conditions have been identified that lead to the permeation of ligands into the periplasm without loss of viability or release of the expressed proteins from the cells, but the invention may be carried out without maintenance of the outer membrane. As demonstrated herein Fc domains expressed or anchored candidate binding polypeptides in the periplasmic space the need for maintenance of the outer membrane (as a barrier to prevent the leakage of the biding protein from the cell) to detect bound labeled ligand is removed. As a result, cells expressing binding proteins anchored to the outer (periplasmic) face of the cytoplasmic membrane can be fluorescently labeled simply by incubating with a solution of fluorescently labeled ligand in cells that either have a partially permeabilized membrane or a nearly completely removed outer membrane.

The permeability of the outer membrane of different strains of bacterial hosts can vary widely. It has been shown previously that increased permeability due to OmpF overexpression was caused by the absence of a histone like protein resulting in a decrease in the amount of a negative regulatory mRNA for OmpF translation (Painbeni et al., 1997). Also, DNA replication and chromosomal segregation is known to rely on intimate contact of the replisome with the inner membrane, which itself contacts the outer membrane at numerous points. A preferred host for library screening applications is E. coli ABLEC strain, which additionally has mutations that reduce plasmid copy number.

Treatments such as hyperosmotic shock can improve labeling significantly. It is known that many agents including, calcium ions (Bukau et al., 1985) and even Tris buffer (Irvin et al., 1981) alter the permeability of the outer-membrane. Further, phage infection stimulates the labeling process. Both the filamentous phage inner membrane protein pIII and the large multimeric outer membrane protein pIV can alter membrane permeability (Boeke et al., 1982) with mutants in pIV known to improve access to maltodextrins normally excluded (Marciano et al., 1999). Using the techniques of the invention, comprising a judicious combination of strain, salt and phage, a high degree of permeability may be achieved (Daugherty et al., 1999). Cells comprising anchored or periplasm-associated polypeptides bound to fluorescently labeled ligands can then be easily isolated from cells that express binding proteins without affinity for the labeled ligand using flow cytometry or other related techniques. However, in some cases, it will be desired to use less disruptive techniques in order to maintain the viability of cells. EDTA and Lysozyme treatments may also be useful in this regard.

III. Antibody-Binding Polypeptides

In certain aspects there are methods for identifying antibody Fc domains with a specific affinity for antibody-binding polypeptide such as an Fc receptor. In some embodiments, an Fc domain is engineered to bind one or more specific Fc receptors. Additionally or alternatively, an Fc domain may be engineered so that it does not specifically bind one or more specific Fc receptors.

In certain embodiments, there are compositions comprising a proteinaceous molecule that has been modified relative to a native or wild-type protein.

In some embodiments that proteinaceous compound has been deleted of amino acid residues; in other embodiments, amino acid residues of the proteinaceous compound have been replaced, while in still further embodiments both deletions and replacements of amino acid residues in the proteinaceous compound have been made. Furthermore, a proteinaceous compound may include an amino acid molecule comprising more than one polypeptide entity. As used herein, a "proteinaceous molecule," "proteinaceous composition," "proteinaceous compound," "proteinaceous chain" or "proteinaceous material" generally refers, but is not limited to, a protein of greater than about 200 amino acids or the full length endogenous sequence translated from a gene; a polypeptide of 100 amino acids or greater; and/or a peptide of 3 to 100 amino acids. All the "proteinaceous" terms described above may be used interchangeably herein; however, it is specifically contemplated that embodiments may be limited to a particular type of proteinaceous compound, such as a polypeptide. Furthermore, these terms may be applied to fusion proteins or protein conjugates as well. A protein may include more than one polypeptide. An IgG antibody, for example, has two heavy chain polypeptides and two light chain polypeptides, which are joined to each other through disulfide bonds.

As used herein a "distinct Fc domain" may be defined as a domain that differs from another Fc by as little as one amino acid. Methods for making a library of distinct antibody Fc domains or nucleic acids that encode antibodies are well known in the art and exemplified herein. For example, in some cases Fc domains may be amplified by error prone PCR as exemplified herein. Furthermore, in certain cases a plurality of antibody Fc domains may comprise a stretch (1, 2, 3, 4, 5, 6, 7, 8, 9, 10 or more) amino acids that have been randomized. In certain cases specific mutations may be engineered into Fc domains. For example, in some aspects, residues that are normally glycosylated in an antibody Fc domain may be mutated. Furthermore, in certain aspects, residues that are normally glycosylated (or adjacent residues) may be used as a site for an insertion of 1, 2, 3, 4, 5, 6, 7, 8, 9, 10 or more amino acids. An amino acid insertion may be made at, or adjacent to, a residue corresponding to amino acid 384 of the IgG1 Fc (SEQ ID NO:2). In still further cases, a population of gram negative bacteria according to the invention may be defined as comprising at least about $1 \times 10^3$, $1 \times 10^4$, $1 \times 10^5$, $1 \times 10^6$, $1 \times 10^7$, $1 \times 10^8$, or more distinct antibodies Fc domains. In some specific cases, a population of Gram negative bacterial cells may be produced by a method comprising the steps of: (a) preparing a plurality of nucleic acid sequences encoding a plurality of distinct antibody Fc domains; and (b) transforming a population of Gram negative bacteria with said nucleic acids wherein the Gram negative bacteria comprise a plurality of antibody Fc domains expressed in the periplasm.

A variety of antibody-binding domains (e.g., FcR polypeptides) are known in the art and may be used in the methods and compositions of the invention. For example, in some aspects, an FcR may have specificity for a particular type or subtype of Ig, such as IgA, IgM, IgE or IgG (e.g., IgG1, IgG2a, IgG2b, IgG3 or IgG4). Thus, in some embodiments the antibody-binding domain may be defined as an IgG binding domain. The FcR polypeptide may compries an eukaryotic, prokaryotic, or synthetic FcR domain. For instance, an antibody Fc-binding domain may be defined as a mammalian, bacterial or synthetic binding domain. Some Fc-binding domains for use in the invention include but are not limited to a binding domain from one of the polypeptides of Table 1. For example, an Fc-binding polypeptide may be encoded by an FCGR2A, FCGR2B, FCGR2c, FCGR3A, FCGR3B, FCGR1A, Fcgr1, FCGR2, FCGR2, Fcgr2, Fcgr2, FCGR3, FCGR3, Fcgr3, FCGR3, Fcgr3, FCGRT, mrp4, spa or spg gene. Preferably, an FcR polypeptide for use according to the invention may be an Fc binding region from human FcγRIa, FcγRIIa, FcγRIIb, FcγRIIc, FcγRIIIa, FcγRIIIb, FcαRI or C1q.

In still further embodiments of the invention an Fc polypeptide may be anchored to the inner membrane of a Gram negative bacteria. Methods and compositions for the anchoring of polypeptides to the inner membrane of Gram negative bacterial have previously been described (U.S. Pat. No. 7,094,571 and U.S. Patent Publ. 20050260736). Thus, in some aspects, an Fc domain may be fused to a polypeptide that is associated with or integrated in a bacterial inner membrane. Such a fusion protein may comprise an N terminal or C terminal fusion with an Fc domain and in some case may comprise additional linker amino acids between the membrane anchoring polypeptide and the Fc domain. In certain specific cases, a membrane anchoring polypeptide may be the first six amino acids encoded by the E. coli NlpA gene, one or more transmembrane α-helices from an E. coli inner membrane protein, a gene III protein of filamentous phage or a fragment thereof, or an inner membrane lipoprotein or fragment thereof. Thus, as an example, a membrane anchoring polypeptide may be an inner membrane lipoprotein or fragment thereof such as from AraH, MglC, MalF, MalG, MalC, MalD, RbsC, RbsC, ArtM, ArtQ, GlnP, ProW, HisM, HisQ, LivH, LivM, LivA, LivE, DppB, DppC, OppB, AmiC, AmiD, BtuC, ThuD, FecC, FecD, FecR, FepD, NikB, NikC, CysT, CysW, UgpA, UgpE, PstA, PstC, PotB, PotC, PotH, Pod, ModB, NosY, PhnM, LacY, SecY, TolC, Dsb, B, DsbD, TouB, TatC, CheY, TraB, ExbD, ExbB or Aas.

The skilled artisan will understand that methods for selecting cells based upon their interaction (binding) with an FcR are well known in the art. For example, an FcR may be immobilized on a column or bead (e.g., a magnetic bead) and the bacterial cell binding to the FcR separated by repeated washing of the bead (e.g., magnetic separation) or column. Furthermore, in some aspects a target ligand may be labeled such as with a fluorophor, a radioisotope or an enzyme. Thus, bacterial cells may, in some cases, be selected by detecting a label on a bound FcR. For example, a fluorophore may be used to select cells using fluorescence activated cell sorting (FACS). Furthermore, in some aspects, bacterial cells may be selected based on binding or lack of binding two or more FcR polypeptides. For instance, bacteria may be selected that display antibodies that bind to two FcR polypeptides, wherein each FcR is used to select the bacterial sequentially. Conversely, in certain aspects, bacteria may be selected that display antibody Fc domains that bind to one FcR (such as an FcR comprising a first label) but not to a second FcR (e.g., comprising a second label). The foregoing method may be used, for example, to identify antibody Fc domains that bind to a specific FcR but not a second specific FcR.

In certain embodiments the size of the at least one Fc polypeptide proteinaceous molecule may comprise, but is not limited to, about or at least 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 350, 400, 450, 500, 550, 600, 650, 700, 750, 800, 850, 900, 950, 1000 or greater amino molecule residues, and any range derivable therein. Compounds may include the above-mentioned number of contiguous amino acids from SEQ ID NO:1 (human IgG Fc polypeptide) or from SEQ ID NOs 4-9 and these may be further qualified as having a percent identity or homology to SEQ ID NO:2 or any of SEQ ID NO:4-9 (discussed below). It is contemplated that embodiments with respect to SEQ ID NO:2 may be employed with respect to any other amino acid sequences described herein, and vice versa, if appropriate.

As used herein, an "amino molecule" refers to any amino acid, amino acid derivative or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

A. Modified Proteins and Polypeptides

Embodiments concerns modified proteins and polypeptides, particularly a modified protein or polypeptide that exhibits at least one functional activity that is comparable to the unmodified version, yet the modified protein or polypeptide possesses an additional advantage over the unmodified version, such as provoking ADCC, easier or cheaper to produce, eliciting fewer side effects, and/or having better or longer efficacy or bioavailability. Thus, when the present application refers to the function or activity of "modified protein" or a "modified polypeptide" one of ordinary skill in the art would understand that this includes, for example, a protein or polypeptide that 1) performs at least one of the same activities or has at least one of the same specificities as the unmodified protein or polypeptide, but that may have a different level of another activity or specificity; and 2) possesses an additional advantage over the unmodified protein or polypeptide. Determination of activity may be achieved using assays familiar to those of skill in the art, particularly with respect to the protein's activity, and may include for comparison purposes, for example, the use of native and/or recombinant versions of either the modified or unmodified protein or polypeptide. It is specifically contemplated that embodiments concerning a "modified protein" may be implemented with respect to a "modified polypeptide," and vice versa. In addition to the modified proteins and polypeptides discussed herein, embodiments may involve domains, polypeptides, and proteins described in WO 2008/137475, which is hereby specifically incorporated by reference.

Modified proteins may possess deletions and/or substitutions of amino acids; thus, a protein with a deletion, a protein with a substitution, and a protein with a deletion and a substitution are modified proteins. In some embodiments these modified proteins may further include insertions or added amino acids, such as with fusion proteins or proteins with linkers, for example. A "modified deleted protein" lacks one or more residues of the native protein, but possesses the specificity and/or activity of the native protein. A "modified deleted protein" may also have reduced immunogenicity or antigenicity. An example of a modified deleted protein is one that has an amino acid residue deleted from at least one antigenic region—that is, a region of the protein determined to be antigenic in a particular organism, such as the type of organism that may be administered the modified protein.

Substitutional or replacement variants typically contain the exchange of one amino acid for another at one or more sites within the protein and may be designed to modulate one or more properties of the polypeptide, particularly its effector functions and/or bioavailability. Substitutions may or may not be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

In addition to a deletion or substitution, a modified protein may possess an insertion of residues, which typically involves the addition of at least one residue in the polypeptide. This may include the insertion of a targeting peptide or polypeptide or simply a single residue. Terminal additions, called fusion proteins, are discussed below.

The term "biologically functional equivalent" is well understood in the art and is further defined in detail herein. Accordingly, sequences that have between about 70% and about 80%, or between about 81% and about 90%, or even between about 91% and about 99% of amino acids that are identical or functionally equivalent to the amino acids of a native polypeptide are included, provided the biological activity of the protein is maintained. A modified protein may be biologically functionally equivalent to its native counterpart.

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The following is a discussion based upon changing of the amino acids of a protein to create an equivalent, or even an improved, second-generation molecule. For example, certain amino acids may be substituted for other amino acids in a protein structure with or without appreciable loss of interactive binding capacity with structures such as, for example, binding sites to substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity, as discussed below. A proteinaceous molecule has "homology" or is considered "homologous" to a second proteinaceous molecule if one of the following "homology criteria" is met: 1) at least 30% of the proteinaceous molecule has sequence identity at the same positions with the second proteinaceous molecule; 2) there is some sequence identity at the same positions with the second proteinaceous molecule and at the nonidentical residues, at least 30% of them are conservative differences, as described herein, with respect to the second proteinaceous molecule; or 3) at least 30% of the proteinaceous molecule has sequence identity with the second proteinaceous molecule, but with possible gaps of non-identical residues between identical residues. As used herein, the term "homologous" may equally apply to a region of a proteinaceous molecule, instead of the entire molecule. If the term "homology" or "homologous" is qualified by a number, for example, "50% homology" or "50% homologous," then the homology criteria, with respect to 1), 2), and 3), is adjusted from "at least 30%" to "at least 50%." Thus it is contemplated that there may homology of at least 30%, 35%, 40%, 45%, 50%, 55%, 60%, 65%, 70%, 75%, 80%, 85%, 90%, 95%, or more between two proteinaceous molecules or portions of proteinaceous molecules.

Alternatively, a modified polypeptide may be characterized as having a certain percentage of identity to an unmodified polypeptide or to any polypeptide sequence disclosed herein, including SEQ ID NO:1 or any of SEQ ID NOs:4-9. The percentage identity may be at most or at least 50%, 55%, 60%, 65%, 70%, 75%, 80%, 85%, 90%, 95%, 96%, 97%, 98%, 99% or 100% (or any range derivable therein) between two proteinaceous molecules or portions of proteinaceous molecules. It is contemplated that percentage of identity discussed above may relate to a particular region of a polypeptide compared to an unmodified region of a polypeptide. For instance, a polypeptide may contain a modified or mutant Fc domain that can be characterized based on the identity of the amino acid sequence of the modified or mutant Fc domain to an unmodified or mutant Fc domain from the same species. A modified or mutant human Fc domain characterized, for example, as having 90% identity to an unmodified Fc domain means that 90% of the amino acids in that domain are identical to the amino acids in the unmodified human Fc domain (SEQ ID NO:1).

In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

A variety of Fc receptors to which Fc domains bind are well known in the art and some examples of receptors are listed below in Table 1.

TABLE 1

Selected FcR Polypeptides

| Protein name | Gene name | Description | Organisms | Length (aa) | Reference |
|---|---|---|---|---|---|
| Fc-gamma RII-a (CD32) | FCGR2A | Low affinity immunoglobulin gamma Fc region receptor II-a precursor | *Homo sapiens* (Human) | 317 | (Stuart et al., 1987) |
| Fc-gamma RII-a | FCGR2A | Low affinity immunoglobulin gamma Fc region receptor II-a precursor | *Pan troglodytes* (Chimpanzee) | 316 | |
| Fc-gamma RII-b | FCGR2B | Low affinity immunoglobulin gamma Fc region receptor II-b precursor | *Homo sapiens* (Human) | 310 | (Stuart et al., 1989) |
| Fc-gamma RII-c | FCGR2C | Low affinity immunoglobulin gamma Fc region receptor II-c precursor | *Homo sapiens* (Human) | 323 | (Stuart et al., 1989) |
| Fc-gamma RIIIa | FCGR3A | Low affinity immunoglobulin gamma Fc region receptor III-A precursor | *Homo sapiens* (Human) | 254 | (Ravetch and Perussia, 1989) |
| Fc-gamma RIIIb | FCGR3B | Low affinity immunoglobulin gamma Fc region receptor III-B precursor | *Homo sapiens* (Human) | 233 | (Ravetch and Perussia, 1989) |
| Fc-gamma RI (CD64) | FCGR1A | High affinity immunoglobulin gamma Fc receptor I precursor | *Homo sapiens* (Human) | 374 | (Allen and Seed, 1988) |
| Fc-gamma RI | Fcgr1 | High affinity immunoglobulin gamma Fc receptor I precursor | *Mus musculus* (Mouse) | 404 | (Sears et al., 1990) |
| Fc-gamma RII | FCGR2 | Low affinity immunoglobulin gamma Fc region receptor II precursor | *Bos taurus* (Bovine) | 296 | (Zhang et al., 1994) |
| Fc-gamma RII | FCGR2 | Low affinity immunoglobulin gamma Fc region receptor II precursor | *Cavia porcellus* (Guinea pig) | 341 | (Tominaga et al., 1990) |
| Fc-gamma RII | Fcgr2 | Low affinity immunoglobulin gamma Fc region receptor II precursor | *Mus musculus* (Mouse) | 330 | (Ravetch et al., 1986) |
| Fc-gamma RII | Fcgr2 | Low affinity immunoglobulin gamma Fc region receptor II precursor | *Rattus norvegicus* (Rat) | 285 | (Bocek and Pecht, 1993) |
| Fc-gamma RIII | FCGR3 | Low affinity immunoglobulin gamma Fc region receptor III precursor | *Bos taurus* (Bovine) | 250 | (Collins et al., 1997) |
| Fc-gamma RIII | FCGR3 | Low affinity immunoglobulin gamma Fc region receptor III precursor | *Macaca fascicularis* (Crab eating macaque) (Cynomolgus monkey) | 254 | |

TABLE 1-continued

Selected FcR Polypeptides

| Protein name | Gene name | Description | Organisms | Length (aa) | Reference |
|---|---|---|---|---|---|
| Fc-gamma RIII | Fcgr3 | Low affinity immunoglobulin gamma Fc region receptor III precursor | *Mus musculus* (Mouse) | 261 | (Ravetch et al., 1986) |
| Fc-gamma RIII | FCGR3 | Low affinity immunoglobulin gamma Fc region receptor III precursor | *Sus scrofa* (Pig) | 257 | (Halloran et al., 1994) |
| Fc-gamma RIII | Fcgr3 | Low affinity immunoglobulin gamma Fc region receptor III precursor | *Rattus norvegicus* (Rat) | 267 | (Zeger et al., 1990) |
| FcRn | FCGRT | IgG receptor transporter FcRn large subunit p51 precursor | *Homo sapiens* (Human) | 365 | |
| FcRn | FCGRT | IgG receptor transporter FcRn large subunit p51 precursor | *Macaca fascicularis* (Crab eating macaque) (Cynomolgus monkey) | 365 | |
| FcRn | Fcgrt | IgG receptor transporter FcRn large subunit p51 precursor | *Mus musculus* (Mouse) | 365 | (Ahouse et al., 1993) |
| FcRn | Fcgrt | IgG receptor transporter FcRn large subunit p51 precursor | *Rattus norvegicus* (Rat) | 366 | (Simister and Mostov, 1989) |
| MRP protein | mrp4 | Fibrinogen- and Ig-binding protein precursor | *Streptococcus pyogenes* | 388 | (Stenberg et al., 1992) |
| Protein B | | cAMP factor | *Streptococcus agalactiae* | 226 | (Ruhlmann et al., 1988) |
| protein A | spa | Immunoglobulin G-binding protein A precursor | *Staphylococcus aureus* (strain NCTC 8325) | 516 | (Uhlen et al., 1984) |
| protein A | spa | Immunoglobulin G-binding protein A precursor | *Staphylococcus aureus* | 508 | (Shuttleworth et al., 1987) |
| protein A | spa | Immunoglobulin G-binding protein A precursor | *Staphylococcus aureus* (strain Mu50/ATCC 700699) | 450 | (Kuroda et al., 2001) |
| protein A | spa | Immunoglobulin G-binding protein A precursor | *Staphylococcus aureus* (strain N315) | 450 | (Kuroda et al., 2001) |
| protein G | spg | Immunoglobulin G-binding protein G precursor | *Streptococcus* sp. group G | 448 | (Fahnestock et al., 1986) |
| protein G | spg | Immunoglobulin G-binding protein G precursor | *Streptococcus* sp. group G | 593 | (Olsson et al., 1987) |
| protein H | | Immunoglobulin G-binding protein H precursor | *Streptococcus pyogenes* serotype M1 | 376 | (Gomi et al., 1990) |
| Protein sbi | sbi | Immunoglobulin G-binding protein sbi precursor | *Staphylococcus aureus* (strain NCTC 8325-4) | 436 | (Zhang et al., 1998) |

TABLE 1-continued

Selected FcR Polypeptides

| Protein name | Gene name | Description | Organisms | Length (aa) | Reference |
|---|---|---|---|---|---|
| Allergen Asp fl 1 | | Allergen Asp fl 1 causes an allergic reaction in human. Binds to IgE and IgG | *Aspergillus flavus* | 32 | |
| Allergen Asp fl 2 | | Allergen Asp fl 2 causes an allergic reaction in human. Binds to IgE and IgG | *Aspergillus flavus* | 20 | |
| Allergen Asp fl 3 | | Allergen Asp fl 3 causes an allergic reaction in human. Binds to IgE and IgG | *Aspergillus flavus* | 32 | |
| Fc-epsilon RI | | IgE receptor displayed on Mast cells, Eosinophils and Basophils | *Homo sapiens* (Human) | | |
| Fc-alpha RI (CD86) | | IgA (IgA1, IgA2) receptor displayed on Macrophages | *Homo sapiens* (Human) | | |
| C1q | C1QA NP_057075.1, C1QB NP_000482.3, C1QC NP_758957.1 | C1q is multimeric complex that binds to antibody Fc composed of 6 A chains, 6 B chains and 6 C chains | *Homo sapiens* (Human) | | |

As discussed above, a polypeptide may comprise an aglycosylated antibody Fc domain capable of binding an FcR polypeptide. In some aspects, the aglycosylated Fc domain may be further defined as having a specific affinity for an FcR polypeptide under physiological conditions. For instance an Fc domain may have an equilibrium dissociation constant between about $10^{-6}$ M to about $10^{-9}$ M under physiological conditions. Furthermore in some aspects an aglycosylated Fc domain may be defined as comprising one or more amino acid substitution or insertion relative to a wild-type sequence, such as a human wild-type sequence.

Means of preparing such a polypeptide include those discussed in WO 2008/137475, which is hereby incorporated by reference. One can alternatively prepare such polypeptides directly by genetic engineering techniques such as, for example, by introducing selected amino acid substitutions or insertions into a known Fc background, wherein the insertion or substitution provides an improved FcR binding capability to aglycosylated Fc regions, as discussed above.

In some embodiments, an aglycosylated Fc domain comprises a specific binding affinity for an FcR such as human FcγRIa, FcγRIIa, FcγRIIb, FcγRIIc, FcγRIIIa, FcγRIIIb, FcαRI or C1q. Thus, in some aspects an aglycosylated Fc domain of the invention is defined as an Fc domain with a specific affinity for FcγRIa. Furthermore, such an Fc domain may be defined as having an equilibrium dissociation constant, with respect to FcγRIa binding, of about $10^{-6}$ M to about $10^{-9}$ M under physiological conditions.

B. Modified Antibodies and Proteinaceous Compounds with Heterologous Regions

Embodiments concern an Fc polypeptide proteinaceous compound that may include amino acid sequences from more than one naturally occurring or native polypeptides or proteins. Embodiments discussed above are contemplated to apply to this section, and vice versa. For instance, a modified antibody is one that contains a modified Fc domain with an antigen binding domain. Moreover, the antibody may have two different antigen binding regions, such as a different region on each of the two heavy chains. Alternatively or additionally, in some embodiments, there are polypeptides comprising multiple heterologous peptides and/or polypeptides ("heterologous" meaning they are not derived from the same polypeptide). A proteinaceous compound or molecule, for example, could include a modified Fc domain with a protein binding region that is not from an antibody. In some embodiments, there are polypeptides comprising a modified Fc domain with a protein binding region that binds a cell-surface receptor. These proteinaceous molecule comprising multiple functional domains may be two or more domains chemically conjugated to one another or it may be a fusion protein of two or more polypeptides encoded by the same nucleic acid molecule. It is contemplated that proteins or polypeptides may include all or part of two or more heterologous polypeptides.

Thus, a multipolypeptide proteinaceous compound may be comprised of all or part of a first polypeptide and all or part of a second polypeptide, a third polypeptide, a fourth polypeptide, a fifth polypeptide, a sixth polypeptide, a seventh polypeptide, an eight polypeptide, a ninth polypeptide, a tenth polypeptide, or more polypeptides.

Polypeptides or proteins (including antibodies) having an antigen binding domain or region of an antibody and an aglycosylated Fc domain can be used against any antigen or epitope, including but not limited to proteins, subunits, domains, motifs, and/or epitopes belonging to the following list of targets: 17-IA, 4-1BB, 4Dc, 6-keto-PGF1a, 8-iso-PGF2a, 8-oxo-dG, A1 Adenosine Receptor, A33, ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAM8, ADAM9, ADAMTS, ADAMTS4, ADAMTS5, Addressins, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, Artemin, anti-Id, ASPARTIC, Atrial natriuretic factor, av/b3 integrin, Axl, b2M, B7-1, B7-2, B7-H, B-lymphocyte Stimulator (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMPs, b-NGF, BOK, Bombesin, Bone-derived neurotrophic factor, BPDE, BPDE-DNA, BTC, complement factor 3 (C3), C3a, C4, C5, C5a, C10, CA125, CAD-8, Calcitonin, cAMP, carcinoembryonic antigen (CEA), carcinoma-associated antigen, Cathepsin A, Cathepsin B, Cathepsin C/DPPI, Cathepsin D, Cathepsin E, Cathepsin H, Cathepsin L, Cathepsin O, Cathepsin S, Cathepsin V, Cathepsin X/ZIP, CBL, CCI, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 proteins), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, *Clostridium botulinum* toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor-associated antigen, DAN, DCC, DcR3, DC-SIGN, Decay accelerating factor, des(1-3)-IGF-I (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, Enkephalinase, eNOS, Eot, eotaxin1, EpCAM, Ephrin B2/EphB4, EPO, ERCC, E-selectin, ET-1, Factor IIa, Factor VII, Factor VIIIc, Factor IX, fibroblast activation protein (FAP), Fas, FcR1, FEN-1, Ferritin, FGF, FGF-19, FGF-2, FGF3, FGF-8, FGFR, FGFR-3, Fibrin, FL, FLIP, Flt-3, Flt-4, Follicle stimulating hormone, Fractalkine, FZD1, FZD2, FZD3, FZD4, FZD5, FZD6, FZD7, FZD8, FZD9, FZD10, G250, Gas 6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (Myostatin), GDF-9, GDF-15 (MIC-1), GDNF, GDNF, GFAP, GFRa-1, GFR-alpha1, GFR-alpha2, GFR-alpha3, GITR, Glucagon, Glut 4, glycoprotein IIb/IIIa (GP IIb/IIIa), GM-CSF, gp130, gp72, GRO, Growth hormone releasing factor, Hapten (NP-cap or NIP-cap), HB-EGF, HCC, HCMV gB envelope glycoprotein, HCMV) gH envelope glycoprotein, HCMV UL, Hemopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, High molecular weight melanoma-associated antigen (HMW-MM), HIV gp120, HIV IIIB gp120 V3 loop, HLA, HLA-DR, HM1.24, HMFG PEM, HRG, Hrk, human cardiac myosin, human cytomegalovirus (HCMV), human growth hormone (HGH), HVEM, I-309, IAP, ICAM, ICAM-1, ICAM-3, ICE, ICOS, IFNg, Ig, IgA receptor, IgE, IGF, IGF binding proteins, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, Inhibin, iNOS, Insulin A-chain, Insulin B-chain, Insulin-like growth factor 1, integrin alpha2, integrin alpha3, integrin alpha4, integrin alpha4/beta1, integrin alpha4/beta7, integrin alpha5 (alphaV), integrin alpha5/beta1, integrin alpha5/beta3, integrin alpha6, integrin beta1, integrin beta2, interferon gamma, IP-10, I-TAC, JE, Kallikrein 2, Kallikrein 5, Kallikrein 6, Kallikrein 11, Kallikrein 12, Kallikrein 14, Kallikrein 15, Kallikrein L1, Kallikrein L2, Kallikrein L3, Kallikrein L4, KC, KDR, Keratinocyte Growth Factor (KGF), laminin 5, LAMP, LAP, LAP (TGF-1), Latent TGF-1, Latent TGF-1 bp1, LBP, LDGF, LECT2, Lefty, Lewis-Y antigen, Lewis-Y related antigen, LFA-1, LFA-3, Lfo, LIF, LIGHT, lipoproteins, LIX, LKN, Lptn, L-Selectin, LT-a, LT-b, LTB4, LTBP-1, Lung surfactant, Luteinizing hormone, Lymphotoxin Beta Receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Muc1), MUC18, Muellerian-inhibitin substance, Mug, MuSK, NAIP, NAP, NCAD, N-Cadherin, NCA 90, NCAM, NCAM, Neprilysin, Neurotrophin-3, -4, or -6, Neurturin, Neuronal growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, Parathyroid hormone, PARC, PARP, PBR, PBSF, PCAD, P-Cadherin, PCNA, PDGF, PDGF, PDK-1, PECAM, PEM, PF4, PGE, PGF, PGI2, PGJ2, PIN, PLA2, placental alkaline phosphatase (PLAP), P1GF, PLP, PP14, Proinsulin, Prorelaxin, Protein C, PS, PSA, PSCA, prostate specific membrane antigen (PSMA), PTEN, PTHrp, Ptk, PTN, R51, RANK, RANKL, RANTES, RANTES, Relaxin A-chain, Relaxin B-chain, renin, respiratory syncytial virus (RSV) F, RSV Fgp, Ret, Rheumatoid factors, RLIP76, RPA2, RSK, S100, SCF/KL, SDF-1, SERINE, Serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptors (e.g., T-cell receptor alpha/beta), TdT, TECK, TEM1, TEM5, TEM7, TEM8, TERT, testicular PLAP-like alkaline phosphatase, TfR, TGF, TGF-alpha, TGF-beta, TGF-beta Pan Specific, TGF-beta RI (ALK-5), TGF-beta RII, TGF-beta RIIb, TGF-beta RIII, TGF-beta1, TGF-beta2, TGF-beta3, TGF-beta4, TGF-beta5, Thrombin, Thymus Ck-1, Thyroid stimulating hormone, Tie, TIMP, TIQ, Tissue Factor, TMEFF2, Tmpo, TMPRSS2, TNF, TNF-alpha, TNF-alpha beta, TNF-beta2, TNFc, TNF-RI, TNF-RII, TNFRSF10A (TRAIL R1 Apo-2, DR4), TNFRSF10B (TRAIL R2 DR5, KILLER, TRICK-2A, TRICK-B), TNFRSF10C (TRAIL R3 DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF RI CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3 M68, TR6), TNFRSF7 (CD27), TNFRSF8 (CD30), TNFRSF9 (4-1BB CD137, ILA), TNFRSF21 (DR6), TNFRSF22 (DcTRAIL R2 TNFRH2), TNFRST23 (Dc-TRAIL R1 TNFRH1), TNFRSF25 (DR3 Apo-3, LARD, TR-3, TRAMP, WSL-1), TNFSF10 (TRAIL Apo-2 Ligand, TL2), TNFSF11 (TRANCE/RANK Ligand ODF, OPG Ligand), TNFSF12 (TWEAK Apo-3 Ligand, DR3 Ligand), TNFSF13 (APRIL TALL2), TNFSF13B (BAFF BLYS, TALL1, THANK, TNFSF20), TNFSF14 (LIGHT HVEM Ligand, LTg), TNFSF15 (TL1A/VEGI), TNFSF18 (GITR Ligand AITR Ligand, TL6), TNFSF1A (TNF-a Conectin, DIF, TNFSF2), TNFSF1B (TNF-b LTa, TNFSF1), TNFSF3 (LTb TNFC, p33), TNFSF4 (OX40 Ligand gp34, TXGP1), TNFSF5 (CD40 Ligand CD154, gp39, HIGM1, IMD3, TRAP), TNFSF6 (Fas Ligand Apo-1 Ligand, APT1 Ligand), TNFSF7 (CD27 Ligand CD70), TNFSF8 (CD30 Ligand CD153), TNFSF9 (4-1BB Ligand CD137 Ligand), TP-1, t-PA, Tpo, TRAIL, TRAIL R, TRAIL-R1, TRAIL-R2, TRANCE, transferring receptor, TRF, Trk, TROP-2, TSG, TSLP, tumor-associated antigen CA 125, tumor-associated antigen expressing Lewis Y related carbohydrate, TWEAK, TXB2, Ung, uPAR, uPAR-1, Urokinase, VCAM, VCAM-1, VECAD, VE-Cadherin, VE-cadherin-2, VEFGR-1 (flt-1), VEGF, VEGFR, VEGFR-3 (flt-4), VEGI, VIM, Viral antigens, VLA, VLA-1, VLA-4, VNR integrin, von Willebrands factor, WIF-1, WNT1, WNT2, WNT2B/13, WNT3, WNT3A, WNT4, WNT5A, WNT5B, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, and receptors for hormones and growth factors. In some embodiments, a polypeptide or protein has an antigen binding domain specific for one or more cell surface tumor antigens. Methods and compositions may be employed to target a tumor cell for ADCC.

Fc domains can bind to an FcR, however, it is contemplated that ADCC can be directed not only through an antigen binding domain on the polypeptide containing the Fc domain, but through some other protein binding domain. Consequently, embodiments concern an Fc domain and a heterologous non-antigen binding domain. In certain embodiments, the non-antigen binding domain bind to the cell surface. Therefore, these agents require either chemical conjugation to or fusion with agents/proteins which are capable of binding to specific target cells. Embodiments further include adjoining all or part of an aglycosylated Fc domain to all or part of any of the proteins listed in Table 2. It is contemplated that embodiments include, but are not limited to, the examples provided in Table 2 and the description herein.

TABLE 2

| Protein Genus | Subgenus | Species | Subspecies |
|---|---|---|---|
| 1) Antibodies | Polyclonal Monoclonal | non-recombinant Recombinant | chimeric |

TABLE 2-continued

| Protein Genus | Subgenus | Species | Subspecies |
|---|---|---|---|
| | | | single chain diabody multimeric |
| 2) Ligands for cell-surface receptors | Cytokines/ growth factors | | IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19 |
| | | Cytokines/growth factors for receptor tyrosine kinases | GM-CSF, G-CSF, M-CSF, EGF, VEGF, FGF, PDGF, HGF, GDNF, Trk, AXL, LTK, TIE, ROR, DDR, KLG, RYK, MuSK ligands |
| 3) Non-Ab binding protein for cell-surface molecule | Binders of cell surface proteins | Cluster of differentiation (CD) molecules | |

A ligand for receptor may be employed to target a cell expressing on its surface the receptor for the ligand. Ligands also include, for instance, CD95 ligand, TRAIL, TNF (such as TNF-α. or TNF-β), growth factors, including those discussed above, such as VEGF and cytokines, such as interferons or interleukins and variants thereof.

Embodiments with multiple domains are also contemplated, such as a VEGF Trap fusion protein that includes the second extracellular domain of the VEGF receptor 1 (Flt-1) with the third domain of the VEGF receptor 2 (KDR/FlK-1) and an IgG Fc region.

a. Fusion and Conjugated Proteins

A specialized kind of insertional variant is the fusion protein. This molecule generally has all or a substantial portion of the native molecule, linked at the N- or C-terminus, to all or a portion of a second polypeptide.

Embodiments also concern conjugated polypeptides, such as translated proteins, polypeptides and peptides, that are linked to at least one agent to form a modified protein or polypeptide. In order to increase the efficacy of molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radio-labeled nucleotides, antiviral agents, chelating agents, cytokines, growth factors, and oligo- or poly-nucleotides. By contrast, a reporter molecule is defined as any moiety that may be detected using an assay. Non-limiting examples of reporter molecules which have been conjugated to antibodies include enzymes, radio-labels, haptens, fluorescent labels, phosphorescent molecules, chemiluminescent molecules, chromophores, luminescent molecules, photoaffinity molecules, colored particles or ligands, such as biotin.

Any antibody of sufficient selectivity, specificity or affinity may be employed as the basis for an antibody conjugate. Such properties may be evaluated using conventional immunological screening methodology known to those of skill in the art. Sites for binding to biological active molecules in the antibody molecule, in addition to the canonical antigen binding sites, include sites that reside in the variable domain that can bind pathogens, B-cell superantigens, the T cell co-receptor CD4 and the HIV-1 envelope (Sasso et al., 1989; Shorki et al., 1991; Silvermann et al., 1995; Cleary et al., 1994; Lenert et al., 1990; Berberian et al., 1993; Kreier et al., 1991). In addition, the variable domain is involved in antibody self-binding (Kang et al., 1988), and contains epitopes (idiotopes) recognized by anti-antibodies (Kohler et al., 1989).

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired. Another such example is the formation of a conjugate comprising an antibody linked to a cytotoxic or anti-cellular agent, and may be termed "immunotoxins."

Amino acids such as selectively-cleavable linkers, synthetic linkers, or other amino acid sequences may be used to separate proteinaceous moieties.

IV. Antibody Fc Libraries

Examples of techniques that could be employed in conjunction with embodiments for creation of diverse antibody Fc domains and/or antibodies comprising such domains may employ techniques similar to those for expression of immunoglobulin heavy chain libraries described in U.S. Pat. No. 5,824,520. Previously employed Fc libraries are discussed in WO 2008/137475, which is specifically incorporated by reference.

V. Screening Antibody Fc Domains

There are embodiments involving methods for identifying molecules capable of binding to a particular FcR. They are described herein, as well as in PCT Application WO 2008/137475, which is hereby specifically incorporated by reference in its entirety. The binding polypeptides screened may comprise a large library of diverse candidate Fc domains, or, alternatively, may comprise particular classes of Fc domains (e.g., engineered point mutations or amino acid insertions) selected with an eye towards structural attributes that are believed to make them more likely to bind the target ligand. In one embodiment, the candidate binding protein is an intact antibody, or a fragment or portion thereof comprising an Fc domain.

To identify a candidate Fc domain capable of binding a target ligand, one may carry out the steps of: providing a population of Gram negative bacterial cells that express a distinct antibody Fc domain; admixing the bacteria or phages and at least a first labeled or immobilized target ligand (FcR polypeptide) capable of contacting the antibody and identifying at least a first bacterium expressing a molecule capable of binding the target ligand.

In some aspects of the aforementioned method, the binding between antibody Fc domain and a labeled FcR polypeptide will prevent diffusing out of a bacterial cell. In this way, molecules of the labeled ligand can be retained in the periplasm of the bacterium comprising a permeablized outer membrane. Alternatively, the periplasm can be removed, whereby the Fc domain will cause retention of the bound candidate molecule since Fc domains are shown to associate with the inner membrane. The labeling may then be used to isolate the cell expressing a binding polypeptide capable of binding the FcR polypeptide, and in this way, the gene encoding the Fc domain polypeptide isolated. The molecule capable of binding the target ligand may then be produced in large quantities using in vivo or ex vivo expression methods, and then used for any desired application, for example, for diagnostic or therapeutic applications. Furthermore, it will be understood that isolated antibody Fc domains identified may be used to construct an antibody fragment or full-length antibody comprising an antigen binding domain.

In further embodiments, methods for producing bacteria of the invention, may comprise at least two rounds of selection (step c) wherein the sub-population of bacterial cells obtained in the first round of selection is subjected to at least a second round of selection based on the binding of the candidate antibody Fc domain to an FcR. Furthermore in some aspects the sub-population of bacterial cells obtained in the first round of selection may be grown under permissive conditions prior to a second selection (to expand the total number of cells). Thus, in some aspects, methods may comprise 2, 3, 4, 5, 6, 7, 8, 9, 10 or more rounds of selection. Furthermore, in some aspects, a sub-population of bacterial cells obtained from each round of selection will be grown under permissive conditions before a subsequent round of selection. Cells isolated following one or more such rounds of selection may be subjected to additional rounds of mutagenesis. In some cases, selection will be performed after removing FcR polypeptide that is not bound to the antibody. Furthermore, in some cases the stringency of selection may be modified by adjusting the pH, salt concentration, or temperature of a solution comprising bacteria that display antibodies. Thus, in some aspects, it may be preferred that a bacterial cell of the invention is grown at a sub-physiological temperature such as at about 25° C.

In still further aspects, a method of producing a bacterial cell according to the invention may be further defined as a method of producing a nucleic acid sequence encoding an Fc domain that binds to at least a first FcR. Thus, a bacterial cell produced by the methods herein may be used to clone a nucleic acid sequence encoding the Fc domain having a specific affinity for an FcR polypeptide. Methods for isolating and amplifying such a nucleic acid from a cell for example by PCR are well known in the art and further described below. Thus, a nucleic acid sequence produced by the forgoing methods is included as part of the instant invention. Furthermore, such a sequence may be expressed in a cell to produce an Fc domain having a specific affinity for an FcR. Thus, in some aspects, the invention provides a method for producing an Fc domain having a specific affinity for an FcR. Furthermore, the invention includes antibody Fc domains produced by the methods of the invention. It will be understood however that the antibody Fc domains produced by such a screen may be combine with antibody variable regions that have an affinity for a particular target ligand and these antibodies are also included as part of the invention.

A. Cloning of Fc domain Coding Sequences

The binding affinity of an antibody Fc or other binding protein can, for example, be determined by the Scatchard analysis of Munson & Pollard (1980). Alternatively, binding affinity can be determined by surface plasmon resonance or any other well known method for determining the kinetics and equilibrium constants for protein:protein interactions. After a bacterial cell is identified that produces molecules of the desired specificity, affinity, and/or activity, the corresponding coding sequence may be cloned. In this manner, DNA encoding the molecule can be isolated and sequenced using conventional procedures (e.g., by using oligonucleotide probes that are capable of binding specifically to genes encoding the antibody or binding protein).

Once isolated, the antibody Fc domain DNA may be placed into expression vectors, which can then transfected into host cells such as bacteria. The DNA also may be modified, for example, by the addition of sequence for human heavy and light chain variable domains, or by covalently joining to the immunoglobulin coding sequence all or part of the coding sequence for a non-immunoglobulin polypeptide. In that manner, "chimeric" or "hybrid" binding proteins are prepared to have the desired binding specificity. For instance, an identified antibody Fc domain may be fused to a therapeutic polypeptide or a toxin and used to target cells (in vitro or in vivo) that express a particular FcR.

Chimeric or hybrid Fc domains also may be prepared in vitro using known methods in synthetic protein chemistry, including those involving crosslinking agents. For example, targeted-toxins may be constructed using a disulfide exchange reaction or by forming a thioether bond. Examples of suitable reagents for this purpose include iminothiolate and methyl-4-mercaptobutyrimidate.

It will be understood by those of skill in the art that nucleic acids may be cloned from viable or inviable cells. In the case of inviable cells, for example, it may be desired to use amplification of the cloned DNA, for example, using PCR. This may also be carried out using viable cells either with or without further growth of cells.

B. Labeled Ligands

In one embodiment, an Fc domain is isolated which has affinity for a labeled FcR polypeptide. By permeabilization and/or removal of the periplasmic membrane of a Gram negative bacterium in accordance with the invention, labeled ligands of potentially any size may be screened. In the absence of removal of the periplasmic membrane, it will typically be preferable that the labeled ligand is less that 50,000 Da in size in order to allow efficient diffusion of the ligand across the bacterial periplasmic membrane.

As indicated above, it will typically be desired to provide an FcR polypeptide which has been labeled with one or more detectable agent(s). This can be carried out, for example, by linking the ligand to at least one detectable agent to form a conjugate. For example, it is conventional to link or covalently bind or complex at least one detectable molecule or moiety. A "label" or "detectable label" is a compound and/or element that can be detected due to specific functional properties, and/or chemical characteristics, the use of which allows the ligand to which it is attached to be detected, and/or further quantified if desired. Examples of labels which could be used include, but are not limited to, enzymes, radiolabels, haptens, fluorescent labels, phosphorescent molecules, chemiluminescent molecules, chromophores, luminescent molecules, photoaffinity molecules, colored particles or ligands, such as biotin.

In one embodiment of the invention, a visually-detectable marker is used such that automated screening of cells for the label can be carried out. In particular, fluorescent labels are beneficial in that they allow use of flow cytometry for isolation of cells expressing a desired binding protein or antibody. Examples of agents that may be detected by visualization with an appropriate instrument are known in the art, as are methods for their attachment to a desired ligand (see, e.g., U.S. Pat. Nos. 5,021,236; 4,938,948; and 4,472,509, each incorporated herein by reference). Such agents can include paramagnetic ions; radioactive isotopes; fluorochromes; NMR-detectable substances and substances for X-ray imaging.

Another type of FcR conjugate is where the ligand is linked to a secondary binding molecule and/or to an enzyme (an enzyme tag) that will generate a colored product upon contact with a chromogenic substrate. Examples of such enzymes include urease, alkaline phosphatase, (horseradish) hydrogen peroxidase or glucose oxidase. In such instances, it will be desired that cells selected remain viable. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Molecules containing azido groups also may be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide-binding proteins in crude cell extracts (Owens & Haley, 1987; Atherton et al., 1985). The 2- and 8-azido nucleotides have also been used to map nucleotide-binding domains of purified proteins (Khatoon et al., 1989; King et al., 1989; and Dholakia et al., 1989) and may be used as ligand binding agents.

Labeling can be carried out by any of the techniques well known to those of skill in the art. For instance, FcR polypeptides can be labeled by contacting the ligand with the desired label and a chemical oxidizing agent such as sodium hypochlorite, or an enzymatic oxidizing agent, such as lactoperoxidase. Similarly, a ligand exchange process could be used. Alternatively, direct labeling techniques may be used, e.g., by incubating the label, a reducing agent such as $SNCl_2$, a buffer solution such as sodium-potassium phthalate solution, and the ligand. Intermediary functional groups on the ligand could also be used, for example, to bind labels to a ligand in the presence of diethylenetriaminepentaacetic acid (DTPA) or ethylene diaminetetracetic acid (EDTA).

Other methods are also known in the art for the attachment or conjugation of a ligand to its conjugate moiety. Some attachment methods involve the use of an organic chelating agent such as diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the ligand (U.S. Pat. Nos. 4,472,509 and 4,938,948, each incorporated herein by reference). FcR polypeptides also may be reacted with an enzyme in the presence of a coupling agent such as glutaraldehyde or periodate. Conjugates with fluorescein markers can be prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate. In still further aspects an FcR polypeptide may be fused to a reporter protein such as an enzyme as described supra or a fluorescence protein.

The ability to specifically label periplasmic expressed proteins with appropriate fluorescent ligands also has applications other than library screening. Specifically labeling with fluorescent ligands and flow cytometry can be used for monitoring production of Fc domains during protein manufacturing.

Once an Fc domain has been isolated, it may be desired to link the molecule to at least one agent to form a conjugate to enhance the utility of that molecule. For example, in order to increase the efficacy of Fc domains or antibody molecules as diagnostic or therapeutic agents, it is conventional to link or covalently bind or complex at least one desired molecule or moiety. Such a molecule or moiety may be, but is not limited to, at least one effector or reporter molecule. Effecter molecules comprise molecules having a desired activity, e.g., cytotoxic activity. Non-limiting examples of effector molecules which have been attached to antibodies include toxins, anti-tumor agents, therapeutic enzymes, radio-labeled nucleotides, antiviral agents, chelating agents, cytokines, growth factors, and oligo- or poly-nucleotides. By contrast, a reporter molecule is defined as any moiety which may be detected using an assay. Techniques for labeling such a molecule are known to those of skill in the art and have been described herein above.

Labeled binding proteins such as Fc domains which have been prepared in accordance with the invention may also then be employed, for example, in immunodetection methods for binding, purifying, removing, quantifying and/or otherwise generally detecting biological components such as protein(s), polypeptide(s) or peptide(s). Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle and Ben-Zeev, 1999; Gulbis and Galand, 1993; and De Jager R et al., 1993, each incorporated herein by reference. Such techniques include binding assays such as the various types of enzyme linked immunosorbent assays (ELISAs) and/or radioimmunoassays (RIA) known in the art.

The Fc domain molecules, including antibodies, may be used, for example, in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Abbondanzo et al., 1990).

VI. Automated Screening With Flow Cytometry

In one embodiment of the invention, fluorescence activated cell sorting (FACS) screening or other automated flow cytometric techniques may be used for the efficient isolation of a bacterial cell comprising a labeled ligand bound to an Fc domain. Instruments for carrying out flow cytometry are known to those of skill in the art and are commercially available to the public. Examples of such instruments include FACS Star Plus, FACScan and FACSort instruments from Becton Dickinson (Foster City, Calif.) Epics C from Coulter Epics Division (Hialeah, Fla.) and MOFLO™ from Cytomation (Colorado Springs, Colo.).

Flow cytometric techniques in general involve the separation of cells or other particles in a liquid sample. Typically, the purpose of flow cytometry is to analyze the separated particles for one or more characteristics thereof, for example, presence of a labeled ligand or other molecule. The basis steps of flow cytometry involve the direction of a fluid sample through an apparatus such that a liquid stream passes through a sensing region. The particles should pass one at a time by the sensor and are categorized base on size, refraction, light scattering, opacity, roughness, shape, fluorescence, etc.

Rapid quantitative analysis of cells proves useful in biomedical research and medicine. Apparati permit quantitative multiparameter analysis of cellular properties at rates of several thousand cells per second. These instruments provide the ability to differentiate among cell types. Data are often displayed in one-dimensional (histogram) or two-dimensional (contour plot, scatter plot) frequency distributions of measured variables. The partitioning of multiparameter data files involves consecutive use of the interactive one- or two-dimensional graphics programs.

Quantitative analysis of multiparameter flow cytometric data for rapid cell detection consists of two stages: cell class characterization and sample processing. In general, the process of cell class characterization partitions the cell feature into cells of interest and not of interest. Then, in sample processing, each cell is classified in one of the two categories according to the region in which it falls. Analysis of the class of cells is very important, as high detection performance may be expected only if an appropriate characteristic of the cells is obtained.

Not only is cell analysis performed by flow cytometry, but so too is sorting of cells. In U.S. Pat. No. 3,826,364, an apparatus is disclosed which physically separates particles, such as functionally different cell types. In this machine, a laser provides illumination which is focused on the stream of particles by a suitable lens or lens system so that there is highly localized scatter from the particles therein. In addition, high intensity source illumination is directed onto the stream of particles for the excitation of fluorescent particles in the stream. Certain particles in the stream may be selectively charged and then separated by deflecting them into designated receptacles. A classic form of this separation is via fluorescent-tagged antibodies, which are used to mark one or more cell types for separation.

Other examples of methods for flow cytometry that could include, but are not limited to, those described in U.S. Pat. Nos. 4,284,412; 4,989,977; 4,498,766; 5,478,722; 4,857,451; 4,774,189; 4,767,206; 4,714,682; 5,160,974; and 4,661,913, each of the disclosures of which are specifically incorporated herein by reference.

For the present invention, an important aspect of flow cytometry is that multiple rounds of screening can be carried out sequentially. Cells may be isolated from an initial round of sorting and immediately reintroduced into the flow cytometer and screened again to improve the stringency of the screen. Another advantage known to those of skill in the art is that nonviable cells can be recovered using flow cytometry. Since flow cytometry is essentially a particle sorting technology, the ability of a cell to grow or propagate is not necessary. Techniques for the recovery of nucleic acids from such non-viable cells are well known in the art and may include, for example, use of template-dependent amplification techniques including PCR.

VII. Automated Screening With Flow Cytometry

Nucleic acid-based expression systems may find use, in certain embodiments of the invention, for the expression of recombinant proteins. For example, one embodiment of the invention involves transformation of Gram negative bacteria with the coding sequences for an antibody Fc domain, or preferably a plurality of distinct Fc domains.

VIII. Nucleic Acid-Based Expression Systems

Nucleic acid-based expression systems may find use, in certain embodiments of the invention, for the expression of recombinant proteins. For example, one embodiment of the invention involves transformation of Gram negative bacteria with the coding sequences for an antibody Fc domain, or preferably a plurality of distinct Fc domains.

A. Methods of Nucleic Acid Delivery

Certain aspects of the invention may comprise delivery of nucleic acids to target cells (e.g., gram negative bacteria). For example, bacterial host cells may be transformed with nucleic acids encoding candidate Fc domains potentially capable binding an FcR. In particular embodiments of the invention, it may be desired to target the expression to the periplasm of the bacteria. Transformation of eukaryotic host cells may similarly find use in the expression of various candidate molecules identified as capable of binding a target ligand.

Suitable methods for nucleic acid delivery for transformation of a cell are believed to include virtually any method by which a nucleic acid (e.g., DNA) can be introduced into such a cell, or even an organelle thereof. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); or by agitation with silicon carbide fibers (Kaeppler et al., 1990; U.S. Pat. Nos. 5,302,523 and 5,464,765, each incorporated herein by reference); by desiccation/inhibition-mediated DNA uptake (Potrykus et al., 1985). Through the application of techniques such as these, cells may be stably or transiently transformed.

B. Vectors

Vectors may find use with the current invention, for example, in the transformation of a Gram negative bacterium with a nucleic acid sequence encoding a candidate Fc domain which one wishes to screen for ability to bind a target FcR. In one embodiment of the invention, an entire heterogeneous "library" of nucleic acid sequences encoding target polypeptides may be introduced into a population of bacteria, thereby allowing screening of the entire library. The term "vector" is used to refer to a carrier nucleic acid molecule into which a nucleic acid sequence can be inserted for introduction into a cell where it can be replicated. A nucleic acid sequence can be "exogenous," or "heterologous", which means that it is foreign to the cell into which the vector is being introduced or that the sequence is homologous to a sequence in the cell but in a position within the host cell nucleic acid in which the sequence is ordinarily not found. Vectors include plasmids, cosmids and viruses (e.g., bacteriophage). One of skill in the art may construct a vector through standard recombinant techniques, which are described in Maniatis et al., 1988 and Ausubel et al., 1994, both of which references are incorporated herein by reference.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference).

Naturally, it will be important to employ a promoter and/or enhancer that effectively directs the expression of the DNA segment in the cell type chosen for expression. One example of such promoter that may be used with the invention is the *E. coli* arabinose or T7 promoter. Those of skill in the art of molecular biology generally are familiar with the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

3. Multiple Cloning Sites

Vectors can include a multiple cloning site (MCS), which is a nucleic acid region that contains multiple restriction enzyme sites, any of which can be used in conjunction with standard recombinant technology to digest the vector (see Carbonelli et al., 1999, Levenson et al., 1998, and Cocea, 1997, incorporated herein by reference) "Restriction enzyme digestion" refers to catalytic cleavage of a nucleic acid molecule with an enzyme that functions only at specific locations in a nucleic acid molecule. Many of these restriction enzymes are commercially available. Use of such enzymes is understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Termination Signals

The vectors or constructs prepared in accordance with the present invention will generally comprise at least one termination signal. A "termination signal" or "terminator" is comprised of the DNA sequences involved in specific termination of an RNA transcript by an RNA polymerase. Thus, in certain embodiments, a termination signal that ends the production of an RNA transcript is contemplated. A terminator may be necessary in vivo to achieve desirable message levels.

Terminators contemplated for use in the invention include any known terminator of transcription described herein or known to one of ordinary skill in the art, including but not limited to, for example, rhp dependent or rho independent terminators. In certain embodiments, the termination signal may be a lack of transcribable or translatable sequence, such as due to a sequence truncation.

5. Origins of Replication

In order to propagate a vector in a host cell, it may contain one or more origins of replication sites (often termed "ori"), which is a specific nucleic acid sequence at which replication is initiated.

6. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

C. Host Cells

In the context of expressing a heterologous nucleic acid sequence, "host cell" refers to a prokaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

In particular embodiments of the invention, a host cell is a Gram negative bacterial cell. These bacteria are suited for use with the invention in that they posses a periplasmic space between the inner and outer membrane and, particularly, the aforementioned inner membrane between the periplasm and cytoplasm, which is also known as the cytoplasmic membrane. As such, any other cell with such a periplasmic space could be used in accordance with the invention. Examples of Gram negative bacteria that may find use with the invention may include, but are not limited to, *E. coli, Pseudomonas aeruginosa, Vibrio cholera, Salmonella typhimurium, Shigella flexneri, Haemophilus influenza, Bordotella pertussi, Erwinia amylovora, Rhizobium* sp. The Gram negative bacterial cell may be still further defined as bacterial cell which has been transformed with the coding sequence of a fusion polypeptide comprising a candidate binding polypeptide capable of binding a selected ligand. The polypeptide is anchored to the outer face of the cytoplasmic membrane, facing the periplasmic space, and may comprise an antibody coding sequence or another sequence. One means for expression of the polypeptide is by attaching a leader sequence to the polypeptide capable of causing such directing.

Numerous prokaryotic cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla). Alternatively, bacterial cells such as *E. coli* LE392 could be used as host cells for bacteriophage.

Many host cells from various cell types and organisms are available and would be known to one of skill in the art. Similarly, a viral vector may be used in conjunction with a prokaryotic host cell, particularly one that is permissive for replication or expression of the vector. Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

D. Expression Systems

Numerous expression systems exist that comprise at least a part or all of the compositions discussed above. Such systems could be used, for example, for the production of a polypeptide product identified in accordance with the invention as capable of binding a particular ligand. Prokaryote-based systems can be employed for use with the present invention to produce nucleic acid sequences, or their cognate polypeptides, proteins and peptides. Many such systems are commercially and widely available. Other examples of expression systems comprise of vectors containing a strong prokaryotic promoter such as T7, Tac, Trc, BAD, lambda pL, Tetracycline or Lac promoters, the pET Expression System and an *E. coli* expression system.

E. Candidate Binding Proteins and Antibodies

In certain embodiments, antibody Fc domains are expressed on the cytoplasmic or in the periplasmic space membrane of a host bacterial cell. By expression of a heterogeneous population of such Fc domains, those polypeptides having a high affinity for a target ligand (FcR) may be identified. The identified Fc domains may then be used in various diagnostic or therapeutic applications, as described herein.

As used herein, the term "Fc domain" is intended to refer broadly to any immunoglobulin Fc region such as an IgG, IgM, IgA, IgD or IgE Fc. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

Once an antibody having affinity for a target ligand is identified, the Fc domain may be purified, if desired, using filtration, centrifugation and various chromatographic methods such as HPLC or affinity chromatography. Alternatively, Fc domains, or polypeptides and peptides more generally, can be synthesized using an automated peptide synthesizer.

IX. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Soluble Expression and Purification of Homodimeric Wild Type Fc and Fc2a Fragments All primers and plasmids used in this work are described in Table 1 and Table 2. Fc2a, containing two mutations (S298G/T299A) in the C'E loop of CH2 region, is an aglycosylated Fc domain engineered for binding to the FcγRII family (Sazinsky et al, 2008). It was reported that aglycosylated Fc2a displayed binding affinity to FcγRIIa and FcγRIIb similar to that of wild type glycosylated IgG (Sazinsky et al, 2008). For the soluble expression and secretion of correctly assembled homodimeric Fc fragments (wild type Fc and Fc2a), two plasmids (pDsbA-Fc-FLAG and pDsbA-Fc2a-FLAG) were constructed. pDsbA was generated by digestion of pTrc99A (Amersham Pharmacia) with SalI and FatI restriction endonucleases (compatible with the NcoI) followed by ligation with a synthetic 53 by DsbA signal peptide gene. The parental Fc genes were PCR amplified using the primers STJ#144 and STJ#145, ligated into the pDsbA plasmid using SalI and HindIII restriction enzyme sites to make pDsbA-Fc-FLAG. To generate pDsbA-Fc2a-FLAG the Fc2a gene containing two mutations (S298G/T299A) in the CH2 region was PCR amplified using the two primers (STJ#422 and STJ#147) and the template (pDsbA-Fc-FLAG), and then ligated into SacII/HindIII restriction enzyme treated pDsbA-Fc-FLAG.

For the expression of wild type aglycosylated Fc fragments and aglycosylated Fc2a proteins in *E. coli*, Jude-1 cells (F' [Tn10(Tet$^r$) proAB$^+$ lacI$^q$ Δ(lacZ)M15] mcrA Δ(mrr-hs-dRMS-mcrBC) 80dlacZΔM15 ΔlacX74 deoR recA1 araD139 Δ(ara leu)7697 galU galK rpsL endA1 nupG) (Kawarasaki et al, 2003) harboring pDsbA-Fc-FLAG or pDsbA-Fc2a-FLAG were cultured in 2 L flasks with 500 ml working volume. After 8 hrs expression of aglycosylated Fc or Fc2a and centrifugation at 7,000 rpm for 30 minutes, culture supernatant was filtered through 0.22 μm bottle top filters (Corning, Corning N.Y.) to remove cell debris and then loaded onto a polypropylene column packed with 1 ml of Immobilized Protein A agarose (Pierce, Rockford, Ill.). After loading 400 ml of supernatant, each Protein A agarose column was washed with 75 ml of 20 mM sodium phosphate buffer (pH 7.0) and 50 ml of 40 mM sodium citrate (pH 5.0). The bound antibodies were then eluted with 0.1 M glycine (pH 2.5) and the solution was immediately neutralized by addition of 1 M Tris (pH 8.0) solution. Most of the purified wild type aglycosylated Fc and Fc2a domains assembled into dimers as determined by SDS-PAGE gel analysis (FIG. 1).

Example 2

Production and Purification of Full Length Aglycosylated Trastuzumab and Aglycosylated Trastuzumab-Fc2a For the construction of pSTJ4-Herceptin IgG1-Fc2a, the Fc2a gene was amplified using primers STJ#290 and STJ#291 with pDsbA-Fc2a-FLAG as a template. The amplified PCR fragments were ligated into SalI/EcoRV digested pSTJ4-Herceptin IgG1 (Jung et al, 2010) to generate pSTJ4-Herceptin IgG1-Fc2a. Each of the plasmids for the expression of full length IgG wild type trastuzumab and mutant trastuzumab-Fc2a are designed to be controlled by a lac promoter in a dicistronic operon with N-terminal PelB leader peptide fusions to both heavy and light chains.

*E. coli* BL21(DE3) (EMD Chemicals, Gibbstown, N.J.) transformed with the full length IgG expression plasmids were grown in LB complex medium and then sub-cultured overnight in R/2 medium (Jeong & Lee, 2003). The sub-culture was repeated twice for adaptation in the R/2 defined medium. *E. coli* BL21(DE3) harboring pSTJ4-Herceptin-IgG1 or pSTJ4-Herceptin-IgG1-Fc2a were cultured in 500 ml baffled-flask with 120 ml of R/2 media at 30° C. for 8 h with 250 rpm shaking and then used to inoculate a 3.3 L bench top fermentor (BioFlo310) (New Brunswick Scientific Co., Edison, N.J.) containing 1.2 L R/2 medium. Using a pH-stat glucose feeding strategy, fed-batch fermentations were performed at 30° C. The dissolved oxygen (DO) concentration was continuously monitored and controlled at 40% of air saturation using an automatic cascade control that regulated the agitation speed from 100 rpm to 1,000 rpm, the air flow rate from 1 to 3 SLPM (Standard liquid per minute) and the pure oxygen flow rate from 0 to 1.5 SLPM. The initial pH was set to 6.8 and was automatically adjusted by the supplement of 20% (v/v) ammonium hydroxide at pH less than 6.75 and by the addition of 80% (v/v) feeding solutions when the pH exceeded 6.9 (700 g/L of glucose and 9.77 g/L of $MgSO_4$—$7H_2O$; before induction or 500 g/L glucose, 10 g/L of $MgSO_4$—$7H_2O$, and 100 g/L of yeast extract; after induction). When the OD600 reached approximately 100, the culture temperature was set to 25° C. and following 30 minutes of cooling, protein synthesis was induced by adding isopropyl-1-thio-β-D-galactopyranoside (IPTG) to a concentration of 1 mM. After 7 hours of induction, the culture broth was harvested at an OD600 of approximately 130-140.

The cell pellet was recovered by 30 minutes of centrifugation at 11,000×g and resuspended in 1.2 L of buffer containing 100 mM Tris, 10 mM EDTA (pH 7.4), 4 mg of lysozyme (per g of dry cell weight) and 1 mM PMSF. Incubation with shaking at 250 rpm at 30° C. for 16 h allowed for the release of periplasmic protein. After centrifugation at 14,000×g for 30 minutes to remove cell debris and drop-wise addition of polyethyleneimine (MP Biomedical, Solon, Ohio) to a final concentration of 0.2% (w/v), the solution was centrifuged at 14,000×g for 30 minutes and filtered through 0.2 μm filter to remove nucleic acid-cationic polyethyleneimine polymer complexes. The recovered filtrate was passed through immobilized Protein A agarose resin pre-equilibrated in 20 mM sodium phosphate buffer (pH 7.0) by incubating at 4° C. for 16 hours. Wild type aglycosylated trastuzumab or trastuzumab-Fc2a were similarly purified by washing the resin with 200 ml of 20 mM sodium phosphate buffer (pH 7.0), 200 ml of 40 mM sodium citrate (pH 5.0), and eluting with 15 ml of 0.1 M glycine (pH 3.0) followed by immediate neutralization in 1M Tris (pH 8.0) solution. The Protein A column purified samples were concentrated by ultrafiltration through a 10 kDa MW cutoff membrane, loaded onto a Superdex 200 gel filtration chromatography column, and fully assembled antibodies were collected in PBS (pH 7.4).

Example 3

ELISA Analysis for Fc2a and Full Length Aglycosylated Trastuzumab-Fc2a

Figure 2:
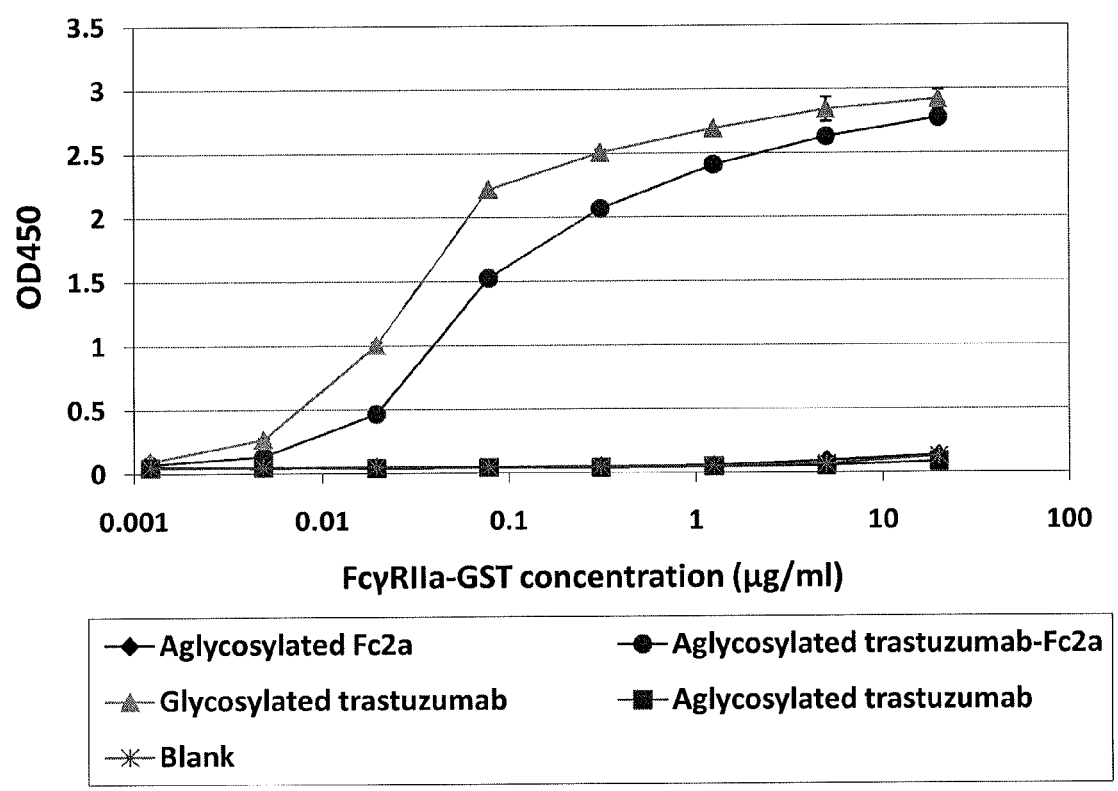
FIG. 2. ELISA assays showing the affinity of aglycosylated Fc2a (Fc fragments) and aglycosylated trastuzumab-Fc2a (full length IgG) to FcγRIIa. [Note: First bar in each group is RI, second is RIIa and third is RIIb]

For homodimeric aglycosylated Fc2a (Fc fragments) or aglycosylated trastuzumab-Fc2a (full length IgG), binding affinity to FcγRIIa-GST was analyzed by ELISA. 50 μl of 4 μg/ml of aglycosylated trastuzumab, aglycosylated trastuzumab-Fc2a, or clinical grade glycosylated IgG trastuzumab diluted in 0.05 M $Na_2CO_3$ buffer (pH 9.6) were coated on 96 well polystyrene ELISA plates (Corning, Corning, N.Y.) by incubating for 16 hr at 4° C. After blocking of the plates with 1×PBS (pH 7.4), 0.5% BSA for 2 hr at room temperature, washing four times with PBS containing 0.05% Tween20 (PBST), incubation with serially diluted FcγRIIa-GST (Berntzen et al, 2005) at room temperature for 1 hour, and four more PBST washes, 1:5,000 diluted anti-GST antibody HRP conjugate (Amersham Pharmacia, Piscataway, N.J.) was added to the plates. Following another four washes, the plates were developed using Ultra-TMB substrate (Pierce, Rockford, Ill.). As expected, the aglycosylated trastuzumab-Fc2a (full length IgG) exhibited similar high binding affinity to FcγRIIa with glycosylated full length trastuzumab IgG as reported in previous work (Sazinsky et al, 2008). In sharp contrast to the full length IgG format, aglycosylated Fc2a (Fc fragment only) did not show significant binding affinity to FcγRIIa-GST suggesting structural and functional roles of Fab arms for the binding of the FcγRIIa receptor to Fc region (FIG. 2).

Example 4

Figure 3:
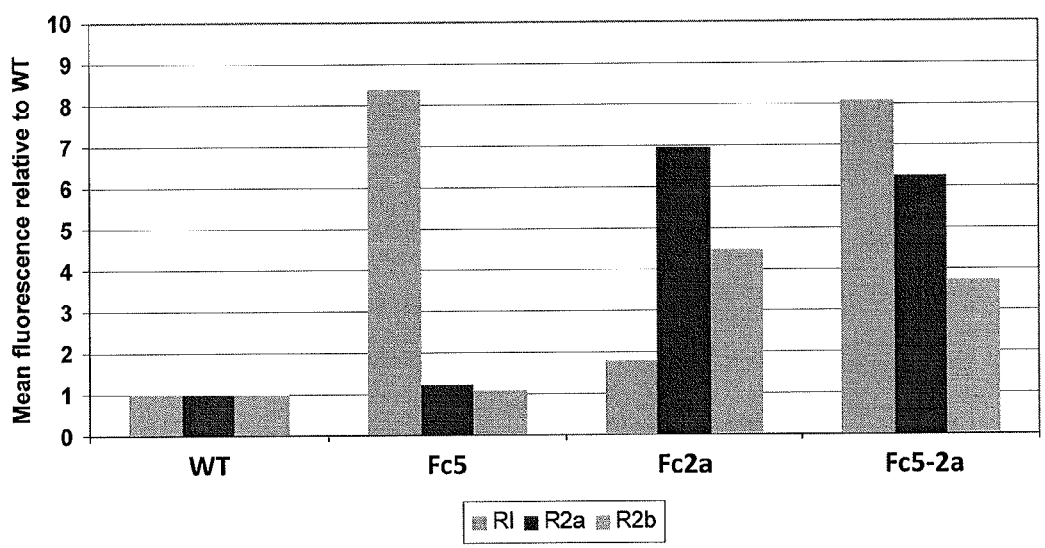
FIG. 3. Specificities of aglycosylated trastuzumab Fc variants in binding to FcγRI, FcγRIIa, and FcγRIIb. [Note: First bar in each group is RI, second is RIIa and third is RIIb]

Isolation of an Aglycosylated Fc Variant Exhibiting High Binding Affinity to all Three FcγRI, FcγRI, and FcγRIIb Aglycosylated trastuzumanb-Fc5 (E382V/M428I; note that the sequence of Fc5 is provided at SEQ ID NO:2) displayed specific high binding affinity to FcγRI (Jung et al, 2010). On the other hand, aglycosylated trastuzumab-Fc2a (S298G/T299A) exhibited high binding affinity to both activating FcγRIIa and inhibitory FcγRIIb (Sazinsky et al, 2008). To investigate the possible activation of both FcγRI and FcγRII by an aglycosylated antibodies, pSTJ4-Herceptin IgG1-Fc5-2a (E382V/M428I/S298G/T299A) was constructed (the sequence of Fc5-2a is provided at SEQ ID NO:3). Fragments of the Fc5-2a gene were amplified using STJ#490 and STJ#220 and digested with SacII/EcoRI restriction enzymes for ligation into pSTJ4-Herceptin IgG1 treated with the same restriction enzymes. After transformation of the constructed expression plasmids into BL21(DE3), full length aglyocsylated trastuzumab-Fc5-2a antibodies were produced by pH-stat fed-batch fermentation. The trastuzumab antibodies were purified from *E. coli* periplasmic proteins by incubating in lysozyme/EDTA containing buffer followed by two sequential chromatography steps, Protein A affinity and size exclusion chromatography as described in example 2. In contrast to trastuzumab-Fc5 and trastuzumab-Fc2a, trastuzumab-Fc5-2a exhibited high affinity to FcγRI as well as FcγRIIa and FcγRIIb (FIG. 3).

Example 5

Construction of Error Prone PCR Library for Engineering Fc5-2a

Figure 4:
FIG. 4. Alignment of X-ray crystal structures of FcγRIIa (PDB: 1FCG) and FcγRIIb (2FCB) showing the high homology between the two proteins.
Figure 5:
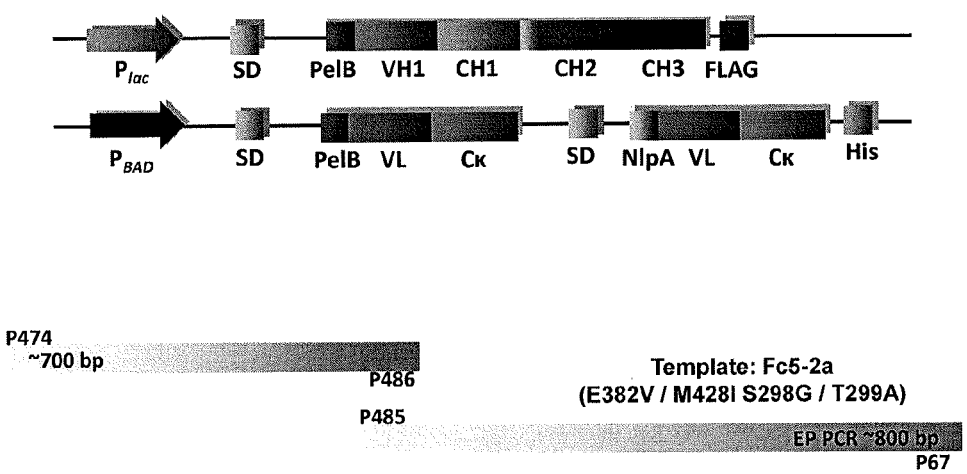

Despite high sequence identity (96%) and sharing similar Fc binding epitopes (FIG. 4), the two receptors (FcγRIIa and FcγRIIa) display opposite functions (Rankin et al, 2006). For selective high binding affinity to activating FcγRIIa over FcγRIIb, a high throughput library screening was performed. An error prone PCR library was created using standard techniques (Fromant et al, 1995). Briefly, the CH2-CH3 region was randomized using the trastuzumab-Fc5-2a as a template and the two primers STJ#485 and STJ#67. VH-CH1 fragments were then PCR amplified using the primers STJ#474 and STJ#486 from the template (pSTJ4-Herceptin IgG). The two fragments, hinge-CH2-CH3 regions and VH-CH1 regions, were assembled by gene assembly PCR using the primers STJ#474 and STJ#67 to generate the trastuzumab heavy chain (VH-CH1-Hinge-CH2-CH3) library as shown in FIG. 5. The amplified heavy chain library genes were ligated into SfiI digested pPe1BFLAG. To enable efficient Fc receptor binding, the resulting plasmids were transformed into *E. coli* Jude-1 harboring the light chain plasmid (pBADPelB-VL-Ck-NlpA-VL-Ck-His), which covalent anchors the IgG light chain (VL-Ck) to the periplasmic side of the inner membrane with an NlpA signal sequence and, at the same time, expresses soluble IgG light chain with a PelB leader peptide to generate tetrameric, covalently anchored, full length IgG. The final library size was 4.8×10⁹ individual transformants with a 0.5% error rate per gene based on the sequencing results of 20 randomly selected library clones.

Example 6

High Throughput FCAS Screening for Selective Binding to FcγRIIa Over FcγRIIb

Figure 7:
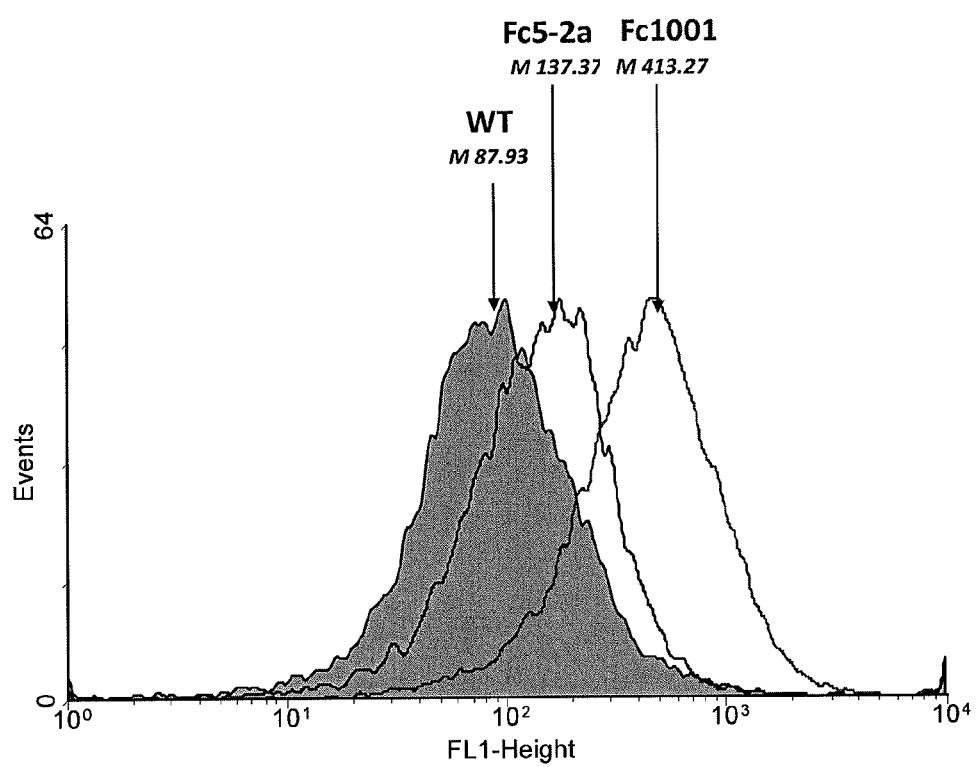
FIG. 7. Histogram showing fluorescence signals of aglycosylated trastuzumab Fc1001 variants in comparison with wild type aglycosylated trastuzumab and aglycosylated trastuzumab Fc5-2a. Spheroplasts were incubated with 20 nM of FcγRIIa-GST-Alexa488 and 100 nM of FcγRIIb-GST for FACS analysis. M: Mean fluorescence intensity.
Figure 8:
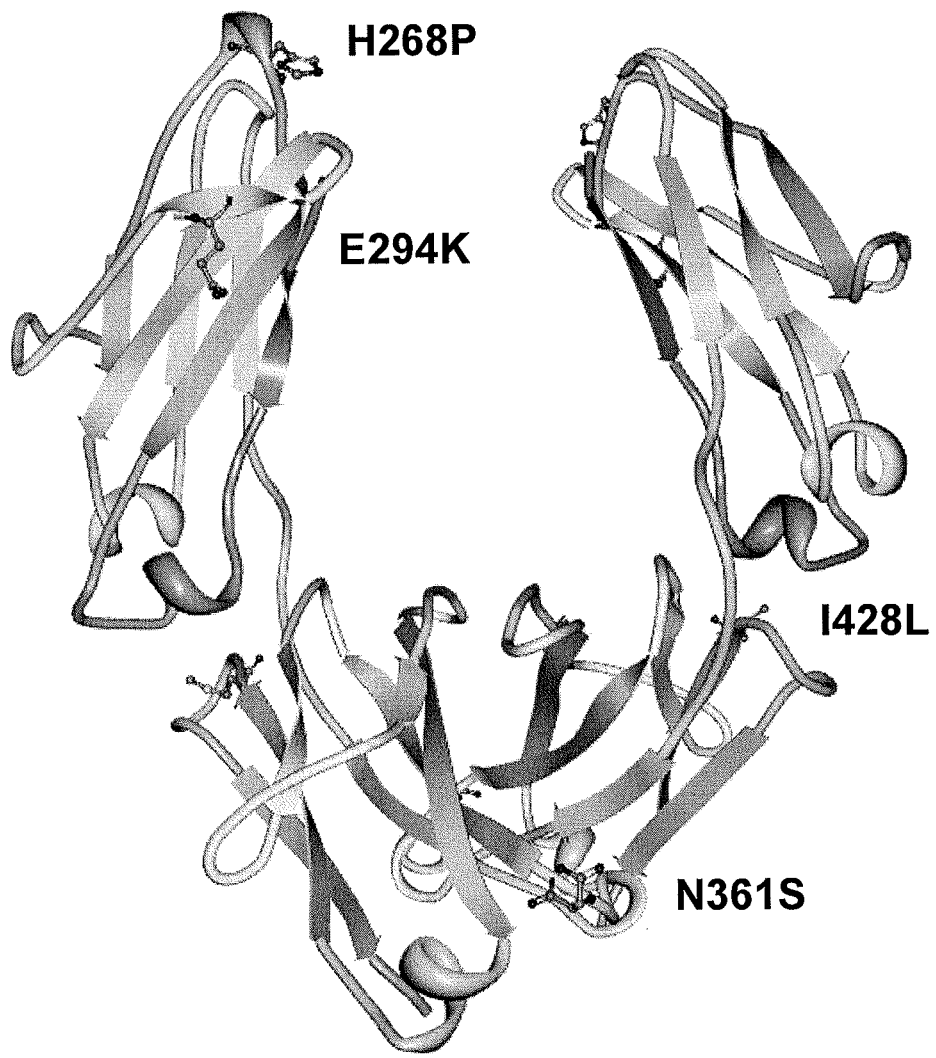
FIG. 8. Mutation points of isolated aglycosylated trastuzumab-Fc1001 represented on the 3D structure of glycosylated IgG (PBD Code: 1FC1).

E. coli Jude-1 cells, co-transformed with both the heavy chain Fc library plasmid (pPelB-VH-CH1-Hinge-CH2-CH3) and the light chain plasmid (pBADPelB-VL-Ck-NlpA-VL-Ck-His), were cultured overnight at 37° C. with 250 rpm shaking in Terrific Broth (Becton Dickinson Diagnostic Systems Difco™, Sparks, Md.) supplemented with 2% (w/v) glucose and appropriate antibiotics (50 µg/ml of chloramphenicol and 50 µg/ml of kanamycin). The overnight cultured cells were diluted 1:100 in 110 ml of fresh Terrific Broth. After incubation at 37° C. for 2 hours and cooling at 25° C. with 250 rpm shaking for 20 minutes, protein expression was induced with 1 mM of isopropyl-1-thio-D-galactopyranoside (IPTG). Following protein expression for 20 hours, 36 ml of the culture broth was harvested by centrifugation, washed two times in 6 ml of cold 10 mM Tris-HCl (pH 8.0) and resuspended in 6 ml of cold STE solution (0.5 M Sucrose, 10 mM Tris-HCl, 10 mM EDTA, pH 8.0). The cell suspension was mixed at 37° C. for 30 minutes, pelleted by centrifugation at 12,000×g for 1 minute and washed in 6 ml of cold Solution A (0.5 M Sucrose, 20 mM MgCl2, 10 mM MOPS, pH 6.8). Incubation of the washed cells in 6 ml of Solution A with 1 mg/ml of hen egg lysozyme at 37° C. for 15 minutes, centrifugation at 12,000×g for 1 minute, and resuspension in 6 ml of cold PBS generated a solution of spheroplasts ready for library screening. To generate fluorescent ligand for fluorescence activated cell sorting (FACS), the extracellular domain of recombinant glycosylated FcγRIIa-GST (Berntzen et al, 2005) was labeled with Alexa488 using an Alexa488 labeling kit (Invitrogen, Carlsbad, Calif.). A competitive screen was used to isolate clones with high binding affinity for FcγRIIa over FcγRIIb in which spheroplasts were incubated with fluorescent FcγRIIa-GST-Alexa488 in excess amounts of non-fluorescent FcγRIIb-GST (concentration of FcγRIIa-GST-Alexa488: concentration of non-fluorescent FcγRIIb-GST=30 nM:100 nM for the 1$^{st}$ round, 10 nM:100 nM for the 2$^{nd}$ round, 10 nM:100 nM for the 3$^{rd}$ round, 5 nM:100 nM for the 4$^{th}$ round, and 5 nM:200 nM for the 5$^{th}$ round of sorting). More than 4×10⁸ spheroplasts were sorted in the first round of screening on a MoFlo flow cytometer (Dako Cytomation, Fort Collins, Colo.) equipped with a 488 nm argon laser for excitation. In each round, the top 3% of the population showing the highest fluorescence is isolated and resorted immediately after the initial sorting. The heavy chain genes (VH-CH1-CH2-CH3) in the spheroplasts were amplified from the collected spheroplasts by PCR with two specific primers STJ#474 and STJ#67, ligated into SfiI restriction enzyme digested pPe1BFLAG-Fc, and transformed in electrocompetent E. coli Jude-1 cells. The resulting transformants were grown on chloramphenicol containing LB agar plates and reprepared as spheroplasts for the next round of sorting as detailed earlier in this example. After the 5$^{th}$ round of sorting, six individual clones were isolated (FIG. 6). Compared to wild type or Fc5-2a aglycosylated trastuzumab, the isolated aglycosylated trastuzumab Fc variants showed significantly higher binding to 20 nM fluorescent FcγRIIa-GST-Alexa488 when in competition with 100 nM of FcγRIIb-GST by FACS (FIG. 7). The Fc1001 aglycosylated trastuzumab exhibiting the highest fluorescence in the FACS analysis contained four mutations (H268P, E294K, N361S, and M428L) in addition to Fc5-2a (FIG. 8).

Example 7

Expression and Purification of Mutant IgGs from HEK293F Cells

Fc1001, Fc1002, Fc1003, Fc1004 (SEQ ID NOs: 4-7, respectively) and Fc2a Fc sequences were amplified by PCR from pPelBFLAG-Fc (STJ#290 and STJ#498) and digested with SalI and XbaI restriction enzymes. These inserts were ligated into the mammalian expression vector pMAZ-IgH-Herceptin prepared from E. coli MC1061. pMAZ-IgH-Herceptin contains the human IgG1 constant domain and the VH domain from traztuzumab. 30 ml cultures containing HEK293F cells (Invitrogen, Carlsbad, Calif.) were transiently transfected with 20 µg of heavy chain containing plasmid (pMAZ-IgH-Herceptin) and 20 µg of light chain containing plasmid (pMAZ-IgL-Herceptin) for 6 days, at which point the cells were removed by centrifugation at 2,000 rpm for 10 minutes. The supernatant was filtered through a 0.45 µm filter and passed through a polypropylene column packed with 1 ml of Immobilized Protein A agarose (Pierce, Rockford, Ill.). The flow through was collected and passed through the column twice more followed by 40 ml of 10 mM Phosphate buffered saline at pH 7.4. The bound antibodies were eluted with 1.7 ml 100 mM glycine HCl at pH 2.7 and then neutralized with 150 ul 1.0 M Tris at pH 8.0. Buffer exchange into 10 mM PBS pH 7.4 was performed using a 15 ml Amicon Ultra spin column (Millipore, Ireland) with a 10 kDa cutoff. Purified antibodies demonstrated near complete assembly when run on an SDS-PAGE gel (FIG. 9).

Example 8

Quantitative Binding Affinity of Mutant IgGs to FcγRIIa and FcγRIIb

Binding of aglycosylated trastuzumab (AglycoT)-Fc2a, Fc1001, Fc1003, and Fc1004 to soluble human FcγRIIa$^{R131}$-GST or FcγRIIb-GST (Berntzen et al, 2005) was analyzed by surface plasmon resonance using a BIAcore 3000 biosensor (Biacore, Piscataway, N.J.). The fully assembled AglycoT-Fc2a, Fc 1001, Fc 1003, and Fc 1004 antibodies were immobilized individually on a CM-5 sensor chip using an amine coupling kit as recommended by the manufacturer. Binding experiments were done in HBS-EP buffer (10 mM HEPES pH 7.4, 150 mM NaCl, 3.4 mM EDTA, and 0.005% P20 surfactant). Either soluble dimeric FcγRIIa-GST or FcγRIIb-GST solutions were injected at flow rate of 30 µl/min for 60 seconds with dissociation time 300 seconds. Regeneration of the ligand was performed by triple injection of 50 mM glycine, pH 4.0, 50 mM glycine, pH 9.5, and 3 M NaCl for 2 minutes each. Affinities of soluble dimeric FcγRIIa-GST with AglycoT-Fc2a, Fc1001, Fc1003, and Fc1004 were obtained by injection of soluble FcγRIIa-GST in duplicate at concentrations of 120, 100, 80, 60, 30 nM, 140, 120, 100, 80, 40 nM, 100, 80, 60, 40, 20 nM, and 120, 100, 80, 60, 30 nM, respectively for 60 seconds at a flow rate of 30 µl/min over immobilized AglycoT-Fc2a, Fc1001, Fc1003, and Fc1004. Affinities of the soluble dimeric FcγRIIb-GST with AglycoT-Fc2a, Fc1001, Fc1003, and Fc1004 were obtained by injection of soluble FcγRIIb-GST in duplicate at concentrations of 400, 300, 200, 100, 50 nM, 300, 200, 100, 80, 40 nM, 120, 100, 80, 60, 30 nM, and 300, 200, 100, 80, 40 nM, respectively for 60 seconds at a flow rate of 30 μl/min over immobilized AglycoT-Fc2a, Fc1001, Fc1003, and Fc1004. The response obtained by flowing sample over a bovine serum albumin-coupled surface as well as the trace with buffer was subtracted from the binding curves. Equilibrium dissociation constants ($K_D$) were determined by fitting of the responses to bivalent analyte fitting model provided by BIAevaluation 3.0 software. The binding affinities returned by the fitting of this model are representative of monomeric receptor interaction despite the use of a dimeric construct in these experiments.

Figure 10:
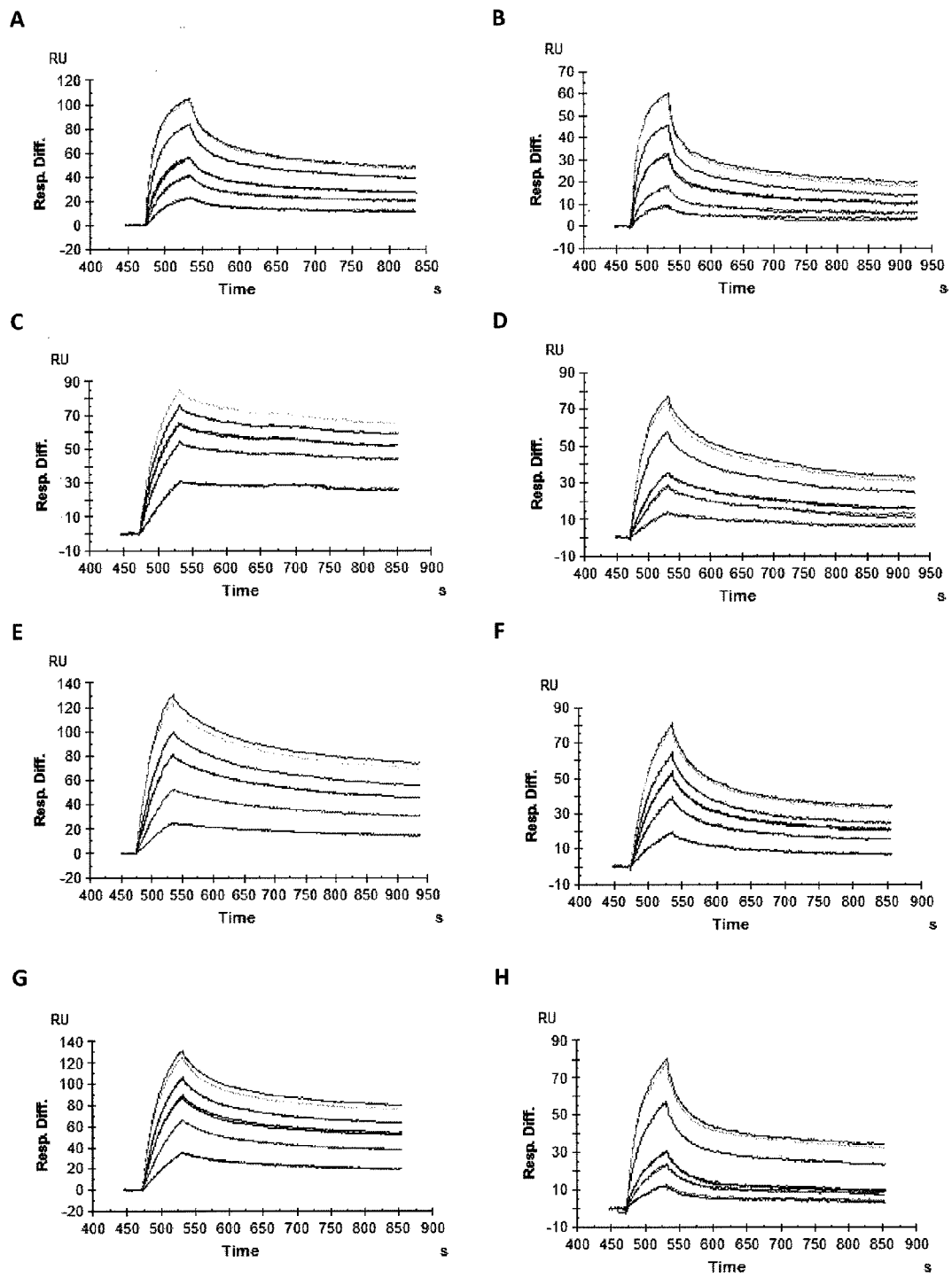
FIG. 10. SPR sensorgrams for aglycosylated trastuzumab format antibodies (AglycoT) of Fc variants to FcγRIIa and FcγRIIb. (A-H) SPR sensorgrams of (A) AglycoT-Fc2a for binding to FcγRIIa-GST, (B) AglycoT-Fc2a for binding to FcγRIIb-GST, (C) AglycoT-Fc1001 for binding to FcγRIIa-GST, (D) AglycoT-Fc1001 for binding to FcγRIIb-GST, (E) AglycoT-Fc 1003 for binding to FcγRIIa-GST, (F) AglycoT-Fc 1003 for binding to FcγRIIb-GST, (G) AglycoT-Fc1004 for binding to FcγRIIa-GST, and (H) AglycoT-Fc1004 for binding to FcγRIIb-GST.

SPR analysis revealed that Fc2a and Fc1004 exhibited high affinities to FcγRIIa with $K_D$ values of 1000 nM and 240 nM, respectively ($k_{on}$, Fc2a=$3.00 \times 10^4$ $M^{-1}$ $sec^{-1}$, $k_{off}$, Fc2a=$3.00 \times 10^{-2}$ $sec^{-1}$; $k_{on}$, Fc1004=$1.46 \times 10^4$ $M^{-1}$ $sec^{-1}$, $k_{off}$, Fc1004=$3.51 \times 10^{-3}$ $sec^{-1}$) (Table 4, FIG. 10). The data indicates that the improvements of affinity for FcγRIIa from Fc2a to Fc1000 series stem from off-rates, while the changes of $K_D$s for FcγRIIb do so from both on and off rates. Dissociation constants of AglycoT format of selected Fc mutants (Fc2a, Fc1001, Fc1003, and Fc1004) were also compared to identify an Fc domain optimized for improved binding to the activating Fc gamma receptor IIa, relative to inhibitory Fc gamma receptor IIb (Table 4). Consequently, AglycoT-Fc1004 showed an enhancement of relative affinity to FcγRIIa over FcγRIIb, 18.5/3.9=4.7 fold compared to AglycoT-Fc2a. No binding to FcγRIIIa has been observed for any of the mutants by ELISA.

Example 9

Figure 11:
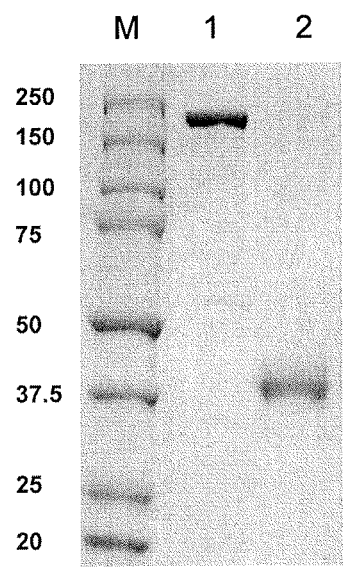
FIG. 11. SDS-PAGE showing the purified FcγRIIb-strep isolated from HEK293F cells. Lane M: molecular weight standard; lane 1: FcγRIIb-strep no denaturing; lane 2: FcγRIIb-strep denatured at 100° C. for 5 minutes.
Figure 12:
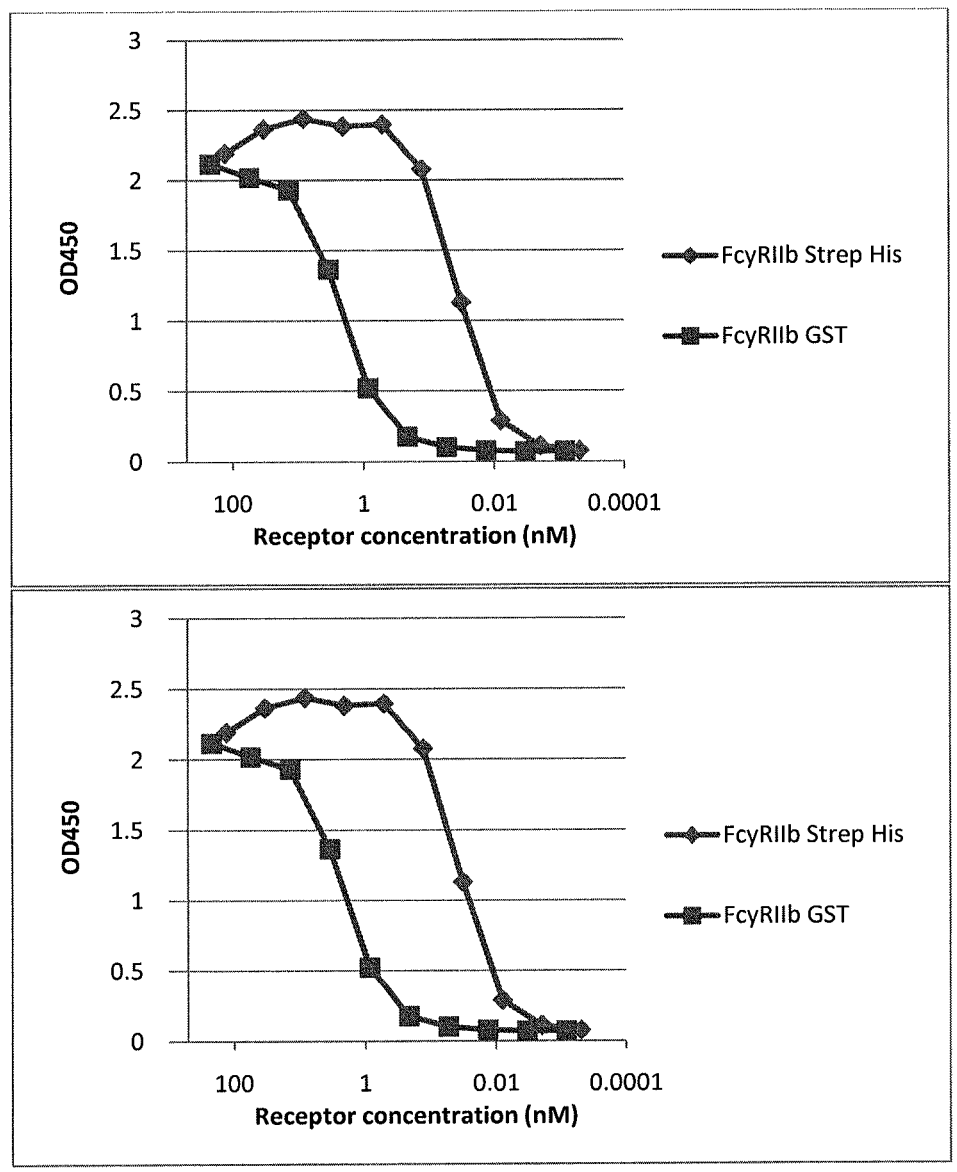
FIG. 12. ELISA assay showing higher affinity of tetrameric FcγRIIb-Strep fusion for human IgG than dimeric FcγRIIb-GST fusion.

Development of an Optimized System for Screening of Aglycosylated Fc Variant IgGs Exhibiting High Binding Affinity to FcγRIIa Over FcγRIIb To further improve mutant binding to FcγRIIa over FcγRIIb higher selection pressure during FACS sorting can be achieved by increasing the apparent affinity of FcγRIIb for IgG through higher order multimerization. For this purpose, a tetrameric FcγRIIb complex with high avidity has been expressed by fusing the C-terminus with the monomer of streptavidin. FcγRIIb was amplified from pSTJ1-FcγRIIb-His (WK#27 and WK#28) and gene assembled with a C-terminal streptavidin monomer amplified from pBAD30-Km-DsbA-FcrRIIIa-Streptavidin-His (WK#29 and WK#30). The complete fragment was digested with BssHII and XbaI for ligation into pMaz-IgH-Herceptin. 40 ug of plasmid was prepared for transient transfection in HEK293F cells (Invitrogen, Carlsbad, Calif.). After expression for 6 days the cells were pelleted by centrifugation at 2000 rpm for 10 minutes. The supernatant was filtered through a 0.45 μm filter and imidazole was added to a final concentration of 10 mM. The solution was passed three times through a polypropylene column containing 1 ml of Nickel NTA resin (Qiagen, Germany) previously equilibrated with PBS containing 20 mM imidazole (pH 8). The column was then washed with 40 ml PBS containing 20 mM imidazole and bound receptor eluted with 2 ml PBS containing 250 mM imidazole at pH 8.0. Buffer exchange into 10 mM PBS pH 7.4 was performed using a 15 ml Amicon Ultra spin column (Millipore, Ireland) with a 10 kDa cutoff. Analysis by SDS-PAGE gel showed formation of the tetramer which was converted to monomeric form upon denaturing at 100 C for 5 minutes (FIG. 11). The affinity of the tetrameric FcγRIIb complex for human IgG was compared to dimeric FcγRIIb-GST by ELISA. 50 μl of 4 μg/ml of clinical grade glycosylated IgG trastuzumab in 0.05 M $Na_2CO_3$ buffer (pH 9.5) was used to coat 96 well polystyrene ELISA plates (Corning, Corning, N.Y.) by incubating for 16 hr at 4° C. After blocking of the plates with 1×PBS (pH 7.4) supplemented with 1% non-fat milk powder for 2 hr at room temperature and washing three times with PBS containing 0.05% Tween20, the plates were incubated with either serially diluted FcγRIIb-GST (Berntzen et al, 2005) or FcγRIIb-Strep at room temperature for 1 h. The plates were washed six times with 1×PBST and 1:5,000 diluted anti-ECS antibody HRP conjugate (Bethyl Laboratories, TX, USA) was added. After six washes again, the plates were developed using Ultra-TMB substrate (Pierce, Rockford, Ill.). After ELISA development, the tetrameric complex showed significantly higher affinity than the dimeric construct and should be suitable for FACS screening (FIG. 12).

Example 10

Sequences of Selected Fc Region for Aglycosylated Trastuzumab Fc Variants Exhibiting High Affinity to FcγRIIa Over FcγRIIb Aglycosylated trastuzumab Fc variants showing high affinity to FcγRIIa over FcγRIIb have several substitution mutations as compared to the wild type sequence of the Fc domain (Protein Sequence #1). Fc region sequences for the isolated mutants (Protein Sequence #2, 3, 4, 5, 6, 7, and 8) are summarized in table 3.

TABLE 1

Primers used in this work.

| Primer Name | Primer nucleotide sequence (5' → 3') |
|---|---|
| STJ#67 | AATTCGGCCCCCGAGGCCCCTTTACCCGGGGACAGGGAGAGGCTCTTCTGCGTG (SEQ ID NO: 10) |
| STJ#144 | TTTTAGGGGTCGACGACAAAACTCACACATGCCCACCGTG (SEQ ID NO: 11) |
| STJ#145 | TTTAAGGGAAGCTTCTATTAGGCGCGCCCTTTGTCATCG (SEQ ID NO: 12) |
| STJ#147 | GGCAAATTCTGTTTTATCAGACCGCTTCTG (SEQ ID NO: 13) |
| STJ#220 | CAATTTTGTCAGCCGCCTGAGCAGAAG (SEQ ID NO: 14) |

TABLE 1-continued

Primers used in this work.

| Primer Name | Primer nucleotide sequence (5' → 3') |
|---|---|
| STJ#290 | TTTTAGGGGTCGACAAGAAAGTTGAGCCCAAATCTTGTGACAAAACTCACACATGCCCACCG (SEQ ID NO: 15) |
| STJ#291 | GGCCACCGGATATCTTATTATTTACCCGGGGACAGGGAGAGG (SEQ ID NO: 16) |
| STJ#422 | CTAGGGAGCCGCGGGAGGAGCAGTACAACGGCGCGTACCGTGTGGTCAGCGTCCTC (SEQ ID NO: 17) |
| STJ#474 | CGCAGCGAGGCCCAGCCGGCCATGGCGGAGGTTCAATTAGTGGAATCTG (SEQ ID NO: 18) |
| STJ#485 | CGACAAGAAAGTTGAGCCCAAATCTTGTG (SEQ ID NO: 19) |
| STJ#486 | CACAAGATTTGGGCTCAACTTTCTTGTCG (SEQ ID NO: 20) |
| STJ#498 | TTTTAGGGTCT AGA TCATTTACCCGGGGACAGGGAGAGG (SEQ ID NO: 21) |
| WK#27 | CTCTCCACAGGCGCGCACTCCACACCTGCAGCTCCCCCAAAGG (SEQ ID NO: 22) |
| WK#28 | CTTATCGTCGTCATCCTTGTAGTCAGATCCGGGAGCTTGGACAGTGATGGTCACAG (SEQ ID NO: 23) |
| WK#29 | GGATCTGACTACAAGGATGACGACGATAAGGACCCGTCTAAAGATAGCAAGGCACAAG (SEQ ID NO: 24) |
| WK#30 | ATCAGCGAGCTTCTAGATCATTAGTGGTGATGATGGTGGTGAGAG (SEQ ID NO: 25) |

TABLE 2

Plasmids used in this work.

| Plasmids | Relevant characteristics | Reference or source |
|---|---|---|
| pPelBFLAG | Cm$^r$, lac promoter, tetA gene, skp gene, C-terminal FLAG tag | (Jung et al, 2010) |
| pPelBFLAG-Fc | IgG1-Fc gene in pPelBFLAG | (Jung et al, 2010) |
| pPelBFLAG-Fc5 | IgG1-Fc5 gene in pPelBFLAG | (Jung et al, 2010) |
| pPelBFLAG-Fc2a | IgG1-Fc2a gene in pPelBFLAG | This study |
| pMAZ360-M18.1-Hum-IgG | M18.1 humanized IgG1 gene in pMAZ360 | (Mazor et al, 2007) |
| pSTJ4-Herceptin IgG1 | Trastuzumab IgG1 gene in pMAZ360-M18.1-Hum-IgG1 | (Jung et al, 2010) |
| pSTJ4-Herceptin IgG1-Fc5 | Trastuzumab IgG1-Fc5 gene in pMAZ360-M18.1-Hum-IgG1 | This study |
| pSTJ4-Herceptin IgG1-Fc2a | Trastuzumab IgG1-Fc2a gene in pMAZ360-M18.1-Hum-IgG1 | This study |
| pSTJ4-Herceptin IgG1-Fc5-2a | Trastuzumab IgG1-Fc5-2a gene in pMAZ360-M18.1-Hum-IgG1 | This study |
| pPelB-Herceptin(H)-FLAG | IgG1 heavy chain gene in pPelBFLAG | This study |
| pPelB-Herceptin(H)-Fc5-FLAG | IgG1-Fc5 heavy chain gene in pPelBFLAG | This study |
| pPelB-Herceptin(H)-Fc2a-FLAG | IgG1-Fc2a heavy chain gene in pPelBFLAG | This study |
| pSTJ4-Herceptin IgG1 | Trastuzumab IgG1 gene in pMAZ360-M18.1-Hum-IgG1 | (Jung et al, 2010) |
| pSTJ4-Herceptin IgG1-Fc5 | Trastuzumab IgG1-Fc5 gene in pMAZ360-M18.1-Hum-IgG1 | (Jung et al, 2010) |
| pSTJ4-Herceptin IgG1-Fc2a | Trastuzumba IgG1-Fc2a gene in pMAZ360-M18.1-Hum-IgG1 | This study |
| pSTJ4-Herceptin IgG1-Fc5-2a | Trastuzumba IgG1-Fc5-2a gene in pMAZ360-M18.1-Hum-IgG1 | This study |
| pDsbA | DsbA signal sequence gene in pTrc99A | (Jung et al, 2010) |
| pDsbA-Fc-FLAG | DsbA fused IgG1-Fc gene, C-terminal FLAG tag in pTrc99A | (Jung et al, 2010) |
| pDsbA-Fc5-FLAG | DsbA fused IgG1-Fc5 gene, C-terminal FLAG tag in pTrc99A | This study |
| pDsbA-Fc2a-FLAG | DsbA fused IgG1-Fc2a gene, C-terminal FLAG tag in pTrc99A | This study |
| pBAD30 | Ap$^r$, BAD promoter | (Guzman et al., 1995) |
| pBAD30-KmR | Km$^r$, BAD promoter | (Jung et al., 2007) |
| pBAD-PelB-VL-Ck-NlpA-VL-Ck-His | PelB fused trastuzumab VL-Ck domain and NlpA fused trastuzumab VL-Ck-His in pBAD30-KmR | This study |
| pSTJ1-FcrRIIb-His | hFcγRIIb gene with C-terminus His tag | This study |
| pBAD30-Km-DsbA-FcrRIIIa-Streptavidin-His | hFcγRIIIa gene with C-terminus streptavidin monomer His fusion | This study |

TABLE 2-continued

Plasmids used in this work.

| Plasmids | Relevant characteristics | Reference or source |
|---|---|---|
| pMaz-IgH-Herceptin | Trastuzumab IgG1 heavy chain in pMaz-IgH | (Benhar & Mazor, 2008; U.S. Pubin. 20080292646) |

TABLE 3

Fc region mutations conferring high affinity to FcγRIIa over FcγRIIb

| Fc mutants | Mutations |
|---|---|
| Fc1001 | H268P, S298G, T299A, E294K, N361S, E382V, M428L (SEQ ID NO: 4) |
| Fc1002 | S298G, T299A, N315D, E382V, M428L (SEQ ID NO: 5) |
| Fc1003 | S298G, T299A, K392E, E382V, V397M, M428L (SEQ ID NO: 6) |
| Fc1004 | S298G, T299A, E382V, N390D, M428L (SEQ ID NO: 7) |
| Fc1005 | S298G, T299A, E382V (SEQ ID NO: 8) |
| Fc1006 | V263E, S298G, T299A, E382V (SEQ ID NO: 9) |

TABLE 4

SPR derived disassociation constants for aglycosylated Fc variants to FcγRIIa and FcγRIIb. The kinetic on and off rates were measured by SPR using the bivalent model.

| Ligand[a] | Analyte | $k_{on}$ ($M^{-1} sec^{-1}$) [b] | $k_{off}$ ($sec^{-1}$) [b] | $K_D$ (nM) [b] | $K_D 2b/K_D 2a$ [c] | Chi$^2$ |
|---|---|---|---|---|---|---|
| AglycoT-Fc2a | FcγRIIa-GST | $3.00 \times 10^4$ | $3.00 \times 10^{-2}$ | 1000 | 3.9 | 1.91 |
| | FcγRIIb-GST | $8.78 \times 10^3$ | $3.42 \times 10^{-2}$ | 3895 | | 0.94 |
| AglycoT-Fc1001 | FcγRIIa-GST | $3.46 \times 10^4$ | $3.52 \times 10^{-3}$ | 102 | 9.6 | 0.79 |
| | FcγRIIb-GST | $1.99 \times 10^4$ | $1.94 \times 10^{-2}$ | 975 | | 0.99 |
| AglycoT-Fc1003 | FcγRIIa-GST | $2.03 \times 10^4$ | $7.9 \times 10^{-3}$ | 389 | 3.56 | 1.53 |
| | FcγRIIb-GST | $6.26 \times 10^3$ | $8.66 \times 10^{-3}$ | 1383 | | 1.2 |
| AglycoT-Fc1004 | FcγRIIa-GST | $1.46 \times 10^4$ | $3.51 \times 10^{-3}$ | 240 | 18.5 | 1.67 |
| | FcγRIIb-GST | $2.52 \times 10^3$ | $1.12 \times 10^{-2}$ | 4444 | | 1.82 |

[a] Ligands immobilized on CM5 chip: AglycoT-Fc2a, aglycosylated Fc2a trastuzumab; AglycoT-Fc1001, aglycosylated Fc1001 trastuzumab; AglycoT-Fc1003, aglycosylated Fc1003 trastuzumab; AglycoT-Fc1004, aglycosylated Fc1004 trastuzumab
[b] Note that these constants represent monomeric values due to bivalent analyte fitting.
[c] Ratio of the Kd value for FcγRIIb-GST over FcγRIIa-GST All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,817,837
U.S. Pat. No. 3,826,364
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,284,412
U.S. Pat. No. 4,366,241
U.S. Pat. No. 4,472,509
U.S. Pat. No. 4,498,766
U.S. Pat. No. 4,661,913
U.S. Pat. No. 4,683,195
U.S. Pat. No. 4,683,202
U.S. Pat. No. 4,714,682
U.S. Pat. No. 4,767,206
U.S. Pat. No. 4,774,189
U.S. Pat. No. 4,800,159
U.S. Pat. No. 4,857,451
U.S. Pat. No. 4,883,750
U.S. Pat. No. 4,938,948
U.S. Pat. No. 4,988,618
U.S. Pat. No. 4,989,977
U.S. Pat. No. 5,021,236
U.S. Pat. No. 5,160,974
U.S. Pat. No. 5,302,523
U.S. Pat. No. 5,322,783
U.S. Pat. No. 5,384,253
U.S. Pat. No. 5,464,765
U.S. Pat. No. 5,478,722
U.S. Pat. No. 5,538,877
U.S. Pat. No. 5,538,880
U.S. Pat. No. 5,550,318
U.S. Pat. No. 5,563,055
U.S. Pat. No. 5,567,326
U.S. Pat. No. 5,580,859
U.S. Pat. No. 5,589,466
U.S. Pat. No. 5,610,042
U.S. Pat. No. 5,656,610
U.S. Pat. No. 5,702,932
U.S. Pat. No. 5,736,524
U.S. Pat. No. 5,779,907
U.S. Pat. No. 5,780,448
U.S. Pat. No. 5,789,215
U.S. Pat. No. 5,824,520
U.S. Pat. No. 5,843,650
U.S. Pat. No. 5,846,709
U.S. Pat. No. 5,846,783
U.S. Pat. No. 5,849,497
U.S. Pat. No. 5,849,546
U.S. Pat. No. 5,849,547
U.S. Pat. No. 5,858,652
U.S. Pat. No. 5,866,366
U.S. Pat. No. 5,882,864
U.S. Pat. No. 5,912,148
U.S. Pat. No. 5,916,776
U.S. Pat. No. 5,916,779
U.S. Pat. No. 5,922,574
U.S. Pat. No. 5,928,905
U.S. Pat. No. 5,928,906
U.S. Pat. No. 5,932,451

U.S. Pat. No. 5,935,825
U.S. Pat. No. 5,939,291
U.S. Pat. No. 5,942,391
U.S. Pat. No. 5,945,100
U.S. Pat. No. 5,981,274
U.S. Pat. No. 5,994,624
U.S. Pat. No. 7,094,571
U.S. Pat. No. 7,094,571
U.S. Patent Publ. 20030180937
U.S. Patent Publ. 20030219870
U.S. Patent Publ. 20050260736
U.S. Patent Publ. 20060173170
U.S. Patent Publ. 20080292646
Abbondanzo et al., *Breast Cancer Res. Treat.*, 16:182(151), 1990.
Ahouse et al., *J. Immunol.*, 151:6076-6088, 1993.
Allen and Seed, *Nucleic Acids Res.*, 16:11824, 1988.
Andersen et al., *Eur. J. Immunol.*, 36:3044-3051, 2006.
Andersen et al., *Eur. J. Immunol.*, 36:3044-3051, 2006.
Antibodies: A Laboratory Manual, Cold Spring Harbor Laboratory, 1988
Atherton et al., *Biol. Reprod.*, 32(1):155-171, 1985.
Ausubel et al., In: *Current Protocols in Molecular Biology*, John, Wiley & Sons, Inc, NY, 1994.
Baneyx and Mujacic, *Nat. Biotechnol.*, 22:1399-1408, 2004.
Bellus, *J. Macromol. Sci. Pure Appl. Chem.*, A31(1): 1355-1376, 1994.
Berntzen et al., *J. Immunol. Methods*, 298:93-104, 2005.
Better et al., *Science*, 240: 1041-10433, 1988.
Bocek and Pecht, *FEBS Lett.*, 331, 86-90, 1993.
Boeke et al., *Mol. Gen. Genet.*, 186, 1982.
Boss et al., *Nucleic Acids Res.*, 12:3791-3806, 1984.
Bowden and Georgiou, *J. Biol. Chem.*, 265:16760-16766, 1990.
Bukau et al., *J. Bacteriol.*, 163:61, 1985.
Burman et al., *J. Bacteriol.*, 112:1364, 1972.
Cabilly et al., *Proc. Natl. Acad. Sci. USA*, 81:3273-3277, 1984.
Carbonelli et al., *FEMS Microbiol Lett.*, 177:75-82. 1999
Chames et al., *Proc. Natl. Acad. Sci. USA*, 97:7969-7974, 2000.
Chen and Okayama, *Mol. Cell. Biol.*, 7(8):2745-2752, 1987.
Cocea, *Biotechniques*, 23(5):814-816, 1997.
Collins et al., *Immunogenetics*, 45:440-443, 1997.
Daugherty et al., *Protein Eng.*, 12:613 621, 1999.
De Jager et al., *Semin. Nucl. Med.*, 23(2):165-179, 1993.
de Kruif and Logtenberg, *J. Biol. Chem.*, 271:7630-7634, 1996.
Decad and Nikaido, *J. Bacteriol.*, 128:325, 1976.
Desai et al., *Cancer Res.*, 58:2417-2425, 1998.
Dholakia et al., *J. Biol. Chem.*, 264(34):20638-20642, 1989.
Doolittle and Ben-Zeev, *Methods Mol Biol,* 109:215-237, 1999.
Eigenbrot et al., *J. Molec. Biol.*, 229:969-995, 1993.
Elbein et al., *Glycobiology*, 13:17 R-27, 2003.
European Appln. 320 308
European Appln. 329 822
Fahnestock et al., *J. Bacteriol.*, 167:870-880, 1986.
Farmer et al., *FEMS Microbiol. Lett.*, 176:11, 1999.
Fechheimer, et al., *Proc Natl. Acad. Sci. USA,* 84:8463-8467, 1987.
Fraley et al., *Proc. Natl. Acad. Sci. USA*, 76:3348-3352, 1979.
Francisco et al., *Proc. Natl. Acad. Sci. USA*, 90:10444-10448, 1993.
Frohman, In: *PCR Protocols: A Guide To Methods And Applications*, Academic Press, N.Y., 1990.
Fromant et al., *Analytical Biochem.*, 224:347-353, 1995.
Fromant et al., *Analytical Biochemistry*, 224:347-353, 1995.
Garinot-Schneider et al., *J. Mol. Biol.*, 260:731-742, 1996.
GB Appln. 2 202 328
Georgiou and Segatori, *Current Opin. Biotech.*, 16:538-545, 2005.
Ghetie and Ward, *Annu. Rev. Immunol.*, 18:739-766, 2000.
Ghetie and Ward, *Annu. Rev. Immunol.*, 18:739-766, 2000.
Gomi et al., *J. Immunol.*, 144:4046-4052, 1990.
Gopal, *Mol. Cell. Biol.*, 5:1188-1190, 1985.
Graham and Van Der Eb, *Virology,* 52:456-467, 1973.
Griffiths and Duncan, *Curr. Opin. Biotechnol.*, 9:102-108, 1998.
Gulbis and Galand, *Hum. Pathol.*, 24(12):1271-1285, 1993.
Guzman et al., *J. Bacteriol.*, 177:4121-30, 1995.
Guzman et al., *J. Bacteriol.*, 177:4121-4130, 1995.
Halloran et al., *J. Immunol.*, 153:2631-2641, 1994.
Harland and Weintraub, *J. Cell Biol.*, 101(3):1094-1099, 1985.
Harvey et al., *J. Immunol. Methods*, 308:43-52, 2006.
Harvey et al., *Proc. Natl. Acad. Sci. USA,* 101, 9193-9198, 2004.
Hayhurst et al., *J. Immunol. Methods*, 276:185-196, 2003.
Hayhurst et al., *J. Immunol. Methods*, 276:185-196, 2003.
Hayhurst et al., *J. Immunol. Methods*, 276:185-196, 2003.
Hobot et al., *J. Bacteriol.,* 160:143, 1984.
Hoogenboom and Winter, *J. Mol. Biol.*, 227:381-388, 1992.
Hoogenboom et al., *Immunotechnology,* 4:1-20, 1998.
Hoover and Lubkowski, *Nucl. Acids Res.*, 30:e43, 2002.
Hoover and Lubkowski, *Nucleic Acids Res.*, 30:e43, 2002.
Innis et al., *Proc. Natl. Acad. Sci. USA,* 85(24):9436-9440, 1988.
Irvin et al, *J. Bacteriol.*, 145:1397, 1981.
Jefferis, *Biotechnol. Prog.*, 21:11-16, 2005.
Jeong and Lee, *Appl. Environ. Microbiol.*, 69:1295-1298, 2003.
Jouenne and Junter, *FEMS Microbiol. Lett.*, 56:313, 1990.
Jung et al., *Biotechnol Bioeng,* 98:39-47, 2007
Jung et al., *Protein Expr. Purif.*, 31:240-246, 2003.
Jung et al., *Proc Natl Acad Sci USA* 107: 604-609, 2010.
Kabat et al., In: *Sequences of Proteins of Immunological Interest*, U.S. Dept. Health and Hum. Serv., Bethesda, Md., 1991.
Kabat et al., In: *Sequences of Proteins of Immunological Interest*, U.S. Dept. of Health and Hum. Serv., Bethesda, 1991.
Kaeppler et al., *Plant Cell Reports*, 9:415-418, 1990.
Kaneda et al., *Science*, 243:375-378, 1989.
Kato et al, *J. Biol. Chem.*, 266:3361-3364, 1991.
Kawarasaki et al., *Nucleic Acids Res.*, 31:e126, 2003.
Khatoon et al., *Ann. Neurol,* 26(2):210-215, 1989.
Kim et al., *Eur. J. Immunol.*, 24:2429-2434, 1994.
King et al., *J. Biol. Chem.*, 264(17):10210-10218, 1989.
Kipriyanov and Little, *Mol. Biotechnol.*, 12:173-201, 1999.
Kjaer et al., *FEBS Lett.*, 431:448-452, 1998.
Knight et al., *Mol. Immunol.*, 32:1271-1281, 1995.
Kohler and Milstein, *Nature*, 256:495-497, 1975.
Kouzarides and Ziff, *Nature,* 336:646-6451, 1988.
Kuroda et al., *Lancet*, 357:1225-1240, 2001.
Kwoh et al., *Proc. Natl. Acad. Sci. USA*, 86:1173, 1989.
Labischinski et al., *J. Bacteriol.*, 162:9, 1985.
Landschulz et al., *Science*, 240:1759-1764, 1988.
Lazar et al., *Proc. Natl. Acad. Sci. USA,* 103:4005-4010, 2006.
Lazar et al., *Proc. Natl. Acad. Sci. USA,* 103:4005-4010, 2006.
Lei et al., *J. Bacteriol.*, 169:4379-4383, 1987.
Levenson et al., *Hum. Gene Ther.*, 9(8):1233-1236, 1998.

Li et al., *J. Mol. Biol.*, 337:743-759, 2004.
Maniatis, et al., Molecular Cloning, A Laboratory Manual, Cold Spring Harbor Press, Cold Spring Harbor, N.Y., 1988.
Marciano et al., *Science*, 284:1516, 1999.
Masaki et al., *Nucleic Acids Res.*, 13:1623-1635, 1985.
Mazor et al., *Nat. Biotech.*, 25(5):563-565, 2007.
Mazor et al., *Nat. Biotech.*, 25:563-5, 2007.
Munson and Pollard, *Anal. Biochem.*, 107:220, 1980.
Nagaoka and Akaike, Protein Engineering, 16: 243-245, 2003.
Nicolau and Sene, *Biochim. Biophys. Acta*, 721:185-190, 1982.
Nicolau et al., *Methods Enzymol.*, 149:157-176, 1987.
Nikaido and Nakae, *Adv. Microb. Physiol.*, 20:163, 1979.
Nikaido and Vaara, *Microbiol. Rev.*, 49:1, 1985.
Nikaido, *J. Bacteriology*, 178(20):5853-5859, 1996.
O'Brien et al., *Protein Expr. Purif.*, 24:43-50, 2002.
Ober et al., *J. Immunol.*, 172:2021-2029, 2004b.
Ober et al., *Proc. Natl. Acad. Sci. USA*, 101:11076-11081, 2004a.
Olsson et al., *Eur. J. Biochem.*, 168:319-324, 1987.
Orlandi et al., *Proc. Natl. Acad. Sci. USA*, 86:3833-3837, 1989.
Osborn et al., *J. Biol. Chem.*, 247:3973-3986, 1972.
Owens and Haley, *Biochem. Biophys. Res. Commun.*, 142(3): 964-971, 1987.
Painbeni et al., *Proc Natl. Acad. Sci. USA*, 94:6712, 1997.
Pavlou and Belsey, *Eur. J. Pharm. Biopharm.*, 59:389-396, 2005.
PCT Appln. PCT/US87/00880
PCT Appln. PCT/US89/01025
PCT Appln. WO 88/10315
PCT Appln. WO 89/06700
PCT Appln. WO 90/07641
PCT Appln. WO 93/06213
PCT Appln. WO 94/09699
PCT Appln. WO 95/06128
Potrykus et al., *Mol. Gen. Genet.*, 199(2):169-177, 1985.
Potter and Haley, *Methods Enzymol*, 91:613-633, 1983.
Purvis et al., *Appl. Environ. Microbiol.*, 71:3761-3769, 2005.
Raghavan and Bjorkman, *Annu. Rev. Cell Dev. Biol.*, 12:181-220, 1996.
Rao and Torriani, *J. Bacteriol.*, 170, 5216, 1988.
Rankin et al., *Blood* 108: 2384-2391, 2006.
Ravetch and Perussia et al., *J. Exp. Med.*, 170:481-497, 1989.
Ravetch et al., *Science*, 234:718-725, 1986.
Rippe, et al., *Mol. Cell. Biol.*, 10:689-695, 1990.
Rodewald, *J. Cell Biol.*, 71:666-669, 1976.
Ruhlmann et al., *FEBS Lett.*, 235:262-266, 1988.
Sambrook et al., In: *Molecular cloning: a laboratory manual*, $2^{nd}$ Ed., Cold Spring Harbor Laboratory Press, Cold Spring Harbor, N.Y., 1989.
Sazinsky et al., *Proc. Natl. Acad. Sci. USA*, 105:20167-20172, 2008.
Schierle et al., *J. Bacteriol.*, 185:5706-5713, 2003.
Sears et al., *J. Immunol.*, 144:371-378, 1990.
Sergina and Moasser, *Trends in Molec. Med.*, 13:527-534, 2007.
Sergina, and Moasser, *Trends in Molec. Med.*, 13:527-534, 2007.
Shields et al., *J. Biol. Chem.*, 276:6591-6604, 2001.
Shuttleworth et al., *Gene*, 58(2-3):283-295, 1987.
Simister and Mostov, *Nature*, 337(6203):184-187, 1989.
Sondermann et al., *J. Mol. Biol.*, 309:737-749, 2001.
Stenberg et al., *Mol. Microbiol.*, 6:1185-1194, 1992.
Stengelin et al., *Embo J.*, 7:1053-1059, 1988.
Stuart et al., *Embo J.*, 8:3657-3666, 1989.
Stuart et al., *J. Exp. Med.*, 166:1668-1684, 1987.
Tominaga et al., *Biochem. Biophys. Res. Commun.*, 168:683-689, 1990.
Uhlen et al., *J. Biol. Chem.*, 259:1695-702, 1984.
Van Wielink and Duine, *Trends Biochem Sci.*, 15:136, 1990.
Wada et al., *J. Biol. Chem.*, 274:17353-17357, 1999.
Walker et al., *Nucleic Acids Res.*, 20(7):1691-1696, 1992.
Wong et al., *Gene*, 10:87-94, 1980.
Wright and Morrison, *Trends Biotech.*, 15:26-32, 1997.
Zeger et al., *Proc. Natl. Acad. Sci. USA*, 87:3425-3429, 1990.
Zhang et al., *Immunogenetics*, 39:423-437, 1994.
Zhang et al., *Microbiology*, 144(Pt 4):985-991, 1998.

---

What is claimed is:

1. A polypeptide comprising an aglycosylated antibody human variant IgG Fc domain capable of binding a human FcγRIIa polypeptide, wherein the Fc domain comprises an S298G and T299A amino acid substitutions at amino acids 298 and 299, wherein the numbering of the residues in the Fc domain is that of the EU index as in Kabat, and further wherein the variant IgG Fc domain comprises at least one additional substitution selected from the group consisting of: a) E382V and V263E; b) E382V, N390D and M428L; c) K392E, E382V, V397M and M428L; d) N315D, E382V and M428L, or e) H268P, E294K, N361S, E382V and M428L.

2. The polypeptide of claim 1, wherein the Fc domain comprises the substitutions S298G, T299A, E382V and V263E.

3. The polypeptide of claim 2, wherein the Fc domain comprises SEQ ID NO:9.

4. The polypeptide of claim 1, wherein the Fc domain comprises the substitutions S298G, T299A, E382V, N390D and M428L.

5. The polypeptide of claim 4, wherein the Fc domain comprises SEQ ID NO:7.

6. The polypeptide of claim 1, wherein the Fc domain comprises the substitutions S298G, T299A, E382V, K392E, V397M and M428L.

7. The polypeptide of claim 6, wherein the Fc domain comprises SEQ ID NO:6.

8. The polypeptide of claim 1, wherein the Fc domain comprises the substitutions S298G, T299A, N315D, E382V, and M428L.

9. The polypeptide of claim 8, wherein the Fc domain comprises SEQ ID NO:5.

10. The polypeptide of claim 1, wherein the Fc domain comprises the substitutions S298G, T299A, H268P, E294K, N361S, E382V and M428L.

11. The polypeptide of claim 10, wherein the Fc domain comprises SEQ ID NO:4.

12. The polypeptide of claim 1, further comprising a non-FcR binding domain.

13. The polypeptide of claim 12, wherein the non-FcR binding domain is an antigen binding site of an antibody.

14. The polypeptide of claim 12, wherein the non-FcR binding region is not an antigen binding site of an antibody.

15. The polypeptide of claim 14, wherein the non-FcR binding region binds a cell-surface protein.

16. The polypeptide of claim 15, wherein the cell-surface protein is a receptor.

17. The polypeptide of claim 16, wherein the receptor is a tyrosine kinase.

18. The polypeptide of claim 17, wherein the non-FcR binding region binds multiple tyrosine kinase receptors.

* * * * *